United States Patent
Cappo et al.

(10) Patent No.: US 7,309,128 B2
(45) Date of Patent: Dec. 18, 2007

(54) AUTOMATED STEREOCAMPIMETER AND RELATED METHOD FOR IMPROVED MEASUREMENT OF THE VISUAL FIELD

(75) Inventors: Anthony P. Cappo, New York, NY (US); Gregory Bennett, New York, NY (US); Matthew D. Orr, Danbury, CT (US); Virginia Lubkin, Bronx, NY (US)

(73) Assignee: Centrofuse Technologies, LLC, New York, NY (US)

( * ) Notice: Subject to any disclaimer, the term of this patent is extended or adjusted under 35 U.S.C. 154(b) by 804 days.

(21) Appl. No.: 10/664,493

(22) Filed: Sep. 18, 2003

(65) Prior Publication Data

US 2004/0057013 A1    Mar. 25, 2004

Related U.S. Application Data

(60) Provisional application No. 60/412,434, filed on Sep. 20, 2002.

(51) Int. Cl.
*A61B 3/02* (2006.01)
(52) U.S. Cl. .................. 351/224; 351/237; 351/246
(58) Field of Classification Search ............. 351/222, 351/224, 237–240, 243, 246
See application file for complete search history.

(56) References Cited

U.S. PATENT DOCUMENTS

| 1,735,005 | A |   | 11/1929 | Kirk ........................... 351/225 |
| RE28,921 | E | * | 8/1976 | Haines et al. ............... 351/224 |
| 4,737,024 | A | * | 4/1988 | Damato ....................... 351/224 |
| 5,550,602 | A | * | 8/1996 | Braeuning .................. 351/243 |
| 5,933,210 | A | * | 8/1999 | Ron ............................ 351/246 |

OTHER PUBLICATIONS

New Lloyd Stereo Campimeter Manual of Technique, Editor: The Bureau of Visual Science, American Optical Company, 4th Ed.

* cited by examiner

*Primary Examiner*—Huy Mai
(74) *Attorney, Agent, or Firm*—R. Neil Sudol; Henry D. Coleman; William J. Sapone

(57) ABSTRACT

In a method for testing the visual field of a patient especially the central visual field, stereoscopic or binocularly displaced fixation images are presented under computer control to the respective eyes of the patient. In addition, a series of test images viewable by only one of the patient's eyes is generated under the control of the computer. The fixation images, one for each eye, are presented on two separate electronic displays, while the test images may be produced on a third display member different from the electronic displays. The computer is programmed to precisely determine a boundary between points corresponding to unseen test images and points corresponding to seen test images, by automatically testing additional points in a region located about the curve and between points corresponding to unseen test images and points corresponding to seen test images.

31 Claims, 22 Drawing Sheets

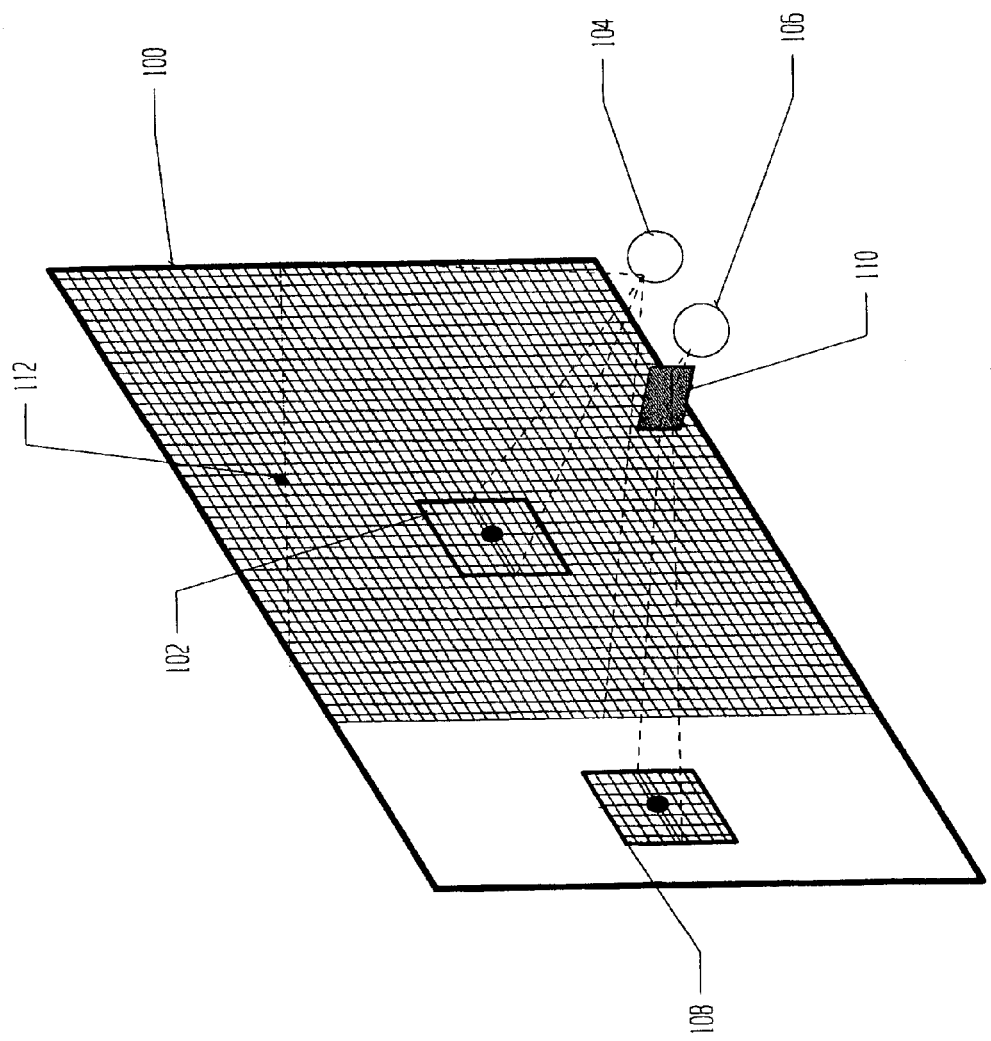

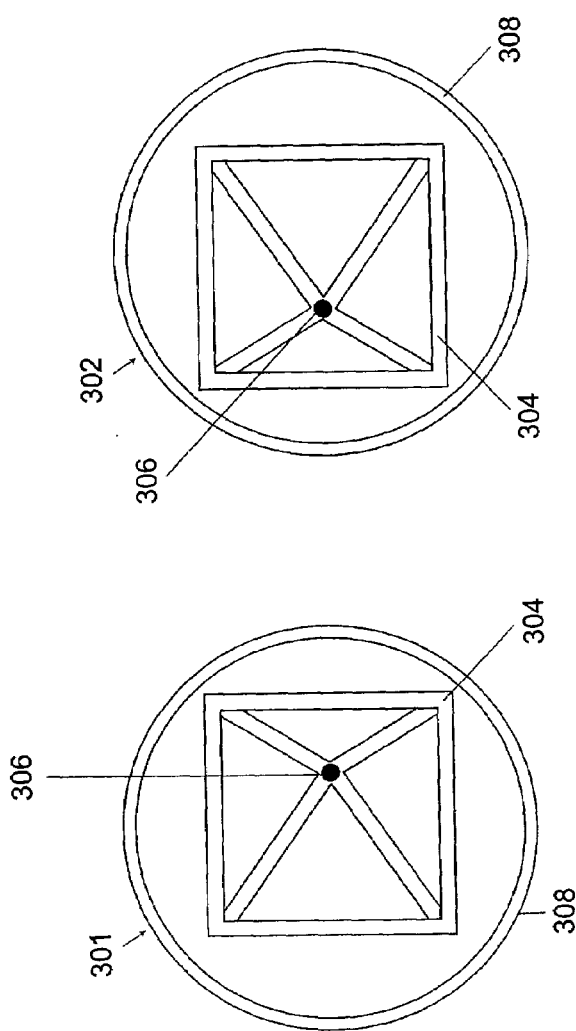
FIGURE 3B
FIGURE 3A
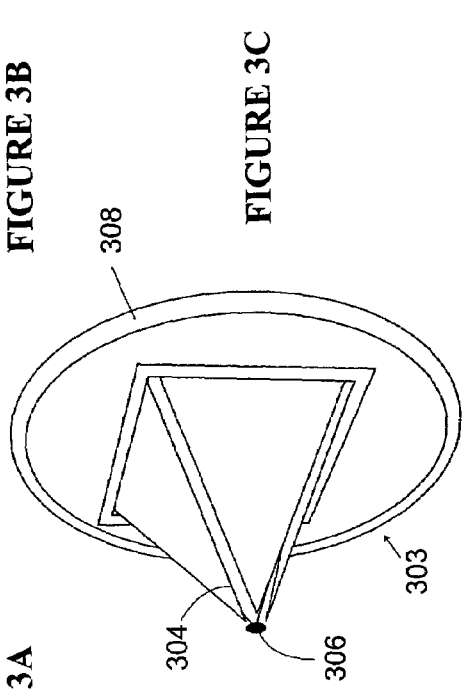
FIGURE 3C

FIGURE 7A
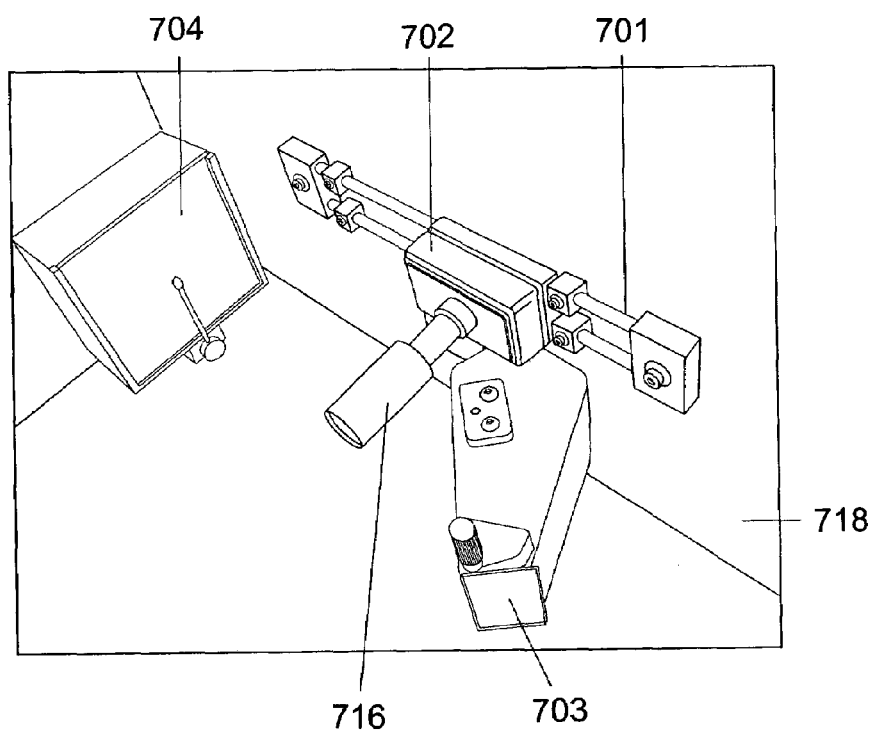
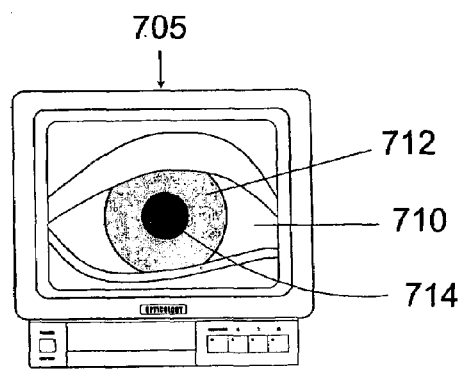
FIGURE 7B
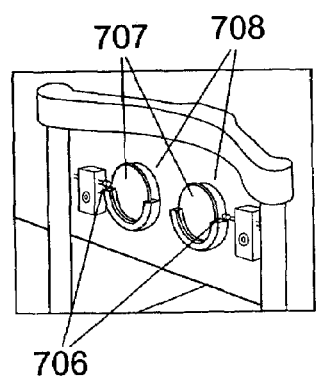
FIGURE 7C

AUTOMATED STEREOCAMPIMETER AND RELATED METHOD FOR IMPROVED MEASUREMENT OF THE VISUAL FIELD

CROSS-REFERENCE TO A RELATED APPLICATION

This application relies for priority purposes on U.S. provisional application No. 60/412,434 filed Sep. 20, 2002.

STATEMENT REGARDING FEDERALLY SPONSORED RESEARCH

This invention and/or underlying inventions were made with Government support under Grant No. R41 EY13341-01 of the National Institutes of Health, Small Business Technology Transfer Program. The Government has certain rights in the invention.

FIELD OF THE INVENTION

This invention relates to a method and an associated apparatus for measuring the visual field, especially the central visual field. The method and the apparatus of the present invention are particularly useful in mapping scotomas, especially central scotomas.

BACKGROUND OF THE INVENTION

Measurements of the visual field are considered very important in ophthalmology in clinical practice and are utilized for following diseases and treatments in glaucoma, diabetes, other vascular diseases, uveitis, retinal detachment, neurological disorders like brain tumors, etc. Visual field examinations test differential light sensitivities at various locations within the visual field of the eye in a subject being tested. The visual field is defined as that portion of space that is visible to the fixated eye.

Perimetric and camperimetric tests are determinations of the character and extent of the indirect field of vision. The campimetric test, however, is confined chiefly to the central and para-central field. Campimetric studies provide a detailed examination of the part of the total visual field that extends within the 30 to 40 degree range of the point of fixation, in the center of the visual field. Studies of this portion of the visual field are especially important in all pathological conditions that affect the retino-cerebral system, and deficiencies of function manifested within this area possess great significance with regard to visual and ocular behavior. This area contains the macular area and the physiological blind spot,. Pathological conditions in the retina result in areas of non-vision or reduced sensitivity of vision, or total loss of vision. These areas of non-vision surrounded by areas of vision can take various shapes and sizes and are called scotomas.

There is no apparatus routinely used that is designed for the study of the field of vision that is capable of rendering an accurate depiction of the visual field when a central scotoma exists, i.e. a pathological area of non-vision that includes the exact center of the field. The primary advantage of the current invention is its ability to accurately map the size and shape of a central scotoma during a central visual field examination by maintaining fixation of the eyes. All known devices that measure visual field are completely dependent upon the patient's capacity to hold the eye steadily fixed upon a central point. If the pathological area of non-vision, or scotoma, covers the center of the field, the patient is unable to see the central fixation point and therefore cannot fixate on it and the device produces incorrect results. These devices, generically called visual field testers or automatic perimeters, are not adequate for testing any portion of the field of vision when a central scotoma exists in the exact center of the field.

Current commercial visual field testing devices are typically of the perimetric type, intended to map the entire visual field including the central field, though recently companies are producing models that measure only the central field but use the same principles as the full-field test. Generally speaking, current commercial visual field testing devices use the inside surface of a hemisphere, which provides for visual field testing with a movable flashing light to map a patient's visual field. In these instruments, the patient is situated in front of the instrument, and one eye is occluded. Each time a light flashes for the eye being tested, the patient indicates that the light is seen by pressing a button. A fixation light is provided in the center of the instrument to keep the patient's visual axis aligned with the instrument. The results are reported in the form of a two-dimensional 'map' of the patient's visual field showing clustered groups of missed light flashes as suspected scotomas or areas of disease. This device maps peripheral scotomas and has generally proven to be accurate, as it employs equipment that objectively monitors the point of fixation of the patient, and keeps a log of when the patient loses fixation on the central fixation target.

However, commercially available visual field testing instruments fail to produce accurate results when the patient has a central scotoma. The obvious problem is that when clinicians want to map such a field, they will ask the patient to stare at the central fixation target, which is impossible for these patients since that is exactly where they are blind. Typically in the case where the scotoma is small and covers the central fixation point, the patient will shift his gaze so he can see the fixation light, in which case he is no longer looking at the fixation light with the center of his vision, and continue with the test. This produces incorrect mapping of the entire field, and a central deficiency is reported as being located off-center when it is not, or can be missed altogether. For patients with a large central scotoma, it is likely that it will be impossible for them to ever see this fixation light and shifting their gaze will not help. A patient with large central scotoma (i.e. 40 degrees in extent) is not a candidate for a commercial visual field tester due to the fact that the patient cannot fixate. Lack of fixation would give each data point on the resulting chart its own random error of offset, depending on the direction of the eye when that point was tested, which would make the results unusable. Therefore, the ability to keep the patient's eye centered and motionless during a test is critical for any visual field-measuring device.

Some manufacturers of commercial instruments have recognized this problem of trying to fixate when an area of non-vision exists at the point of fixation, and have attempted to solve it by providing multiple fixation points arranged in some pattern around but not in the center of vision. The patient is instructed to look in the center of say four fixation points which form a square surrounding the central point of vision. The results of multiple fixation points tends to fail almost as consistently as with one fixation point, since often the scotoma will be large enough that these points cannot be seen either, or the patient may only see three of the four points due to a small scotoma, or it may just be too confusing or tiresome for the patient to bother.

The problems associated with monocular visual field testing was approached in the 1920's by Kirk, who reasoned that if the eye under test had a central scotoma and the other eye did not (which is often the case), the other eye could be used to aid in fixation using binocular vision.

Kirk suggested the use of a central target within the testing area for the eye under test and an identical target to be viewed by the eye not under test. The eye not under test would view the target by way of a mirror placed before it, so that the object was out of the way of the testing arena. He also suggested the use of stereoscopic targets, or one that would appear to have depth when the two images were fused. The eye not under test is able to fixate properly on its own fixation target, if it has no central scotoma, so it holds the eye under test fixated because of the natural tendency to maintain fusion. In this manner, the visual field could be obtained even though the eye under observation is so impaired that it cannot directly see the fixation target.

In the late 1920's and 1930's Lloyd developed a stereo-campimeter, which used the principles in Kirk's U.S. Pat. No. 1,735,005, namely binocular stereoscopic fixation. The instrument was manufactured by American Optical Company and was intended for use at reading distance. The system contained a stereoscope (two images taken from different perspectives) for fixation. The testing arena was a flat area extending 30-40 degrees of the field of vision. The test used a piece of black paper that had non-linear grid lines printed on it representing the curvature of the retina projected on a two-dimensional surface. The eye under test was to look at a central feature on the paper, and the other eye was redirected with a mirror to another surface that had the same central feature and grid lines, yet was displaced slightly relative to the testing arena. Once the two images were aligned with each other it would appear to the patient that he were looking at one fixation point and one set of grid lines which had depth. The examiner would then insert a test object into the field of vision. This was accomplished by a using a white (or colored) sphere (or disc) attached to a thin wire wand. The size of the sphere determined the angular subtense of vision, and the wand was painted black and meant to be invisible. The examiner would insert the test wand throughout the field of vision and ask the patient whether it was visible. If the patient indicated it was not visible, the examiner would mark with a colored pencil on the black paper the points that the patient did not see. The test was painstakingly slow and distracting to the patient, and after complete, the examiner would connect the dots that were not seen obtaining a closed curve representing a scotoma.

Though the technique of stereocampimetry was novel, the device suffered from shortcomings which led to its extinction. The device required a skilled operator to perform the test, and was void of any technology. The patient who was required to concentrate and fix his gaze on the central fixation target while maintaining stereo fusion of the two images, was typically distracted by the examiner's hand coming in and out of the field to mark the points and place the targets. The patient had to be asked if a point was seen and had to respond with a yes or no answer. Since the black paper was illuminated with an incandescent light bulb, the wand was sometimes visible and also caused distraction. Also a significant problem was the time required to take the test, which can fatigue a patient, who is typically elderly with severe vision problems. The resolution of the test is dependent on the number of points the examiner samples would typically be low, and the examiner can never be sure the patient has kept his gaze fixed during the test which would invalidate the data. The other inherent problem with the device deals with the alignment of the stereo targets. If the patient is not fusing the two images, the alignment between the two images needs to be adjusted, which is difficult for the type of patient described above. Also, there were no means to ensure the patient was fixating therefore the test was unreliable.

OBJECTS OF THE INVENTION

It is an object of the present invention to provide an improved visual field testing apparatus and/or an associated method.

A more particular object of the present invention is to provide such an apparatus and/or method that overcomes at least some of the problems inherent in conventional visual field testers, particularly where the patient has a central scotoma.

It is a further object of the present invention to provide such an apparatus and/or method that is easy to use and relatively cost effective.

These and other objects of the present invention will be apparent from the drawings and descriptions herein. Although every object of the invention is attained by at least one embodiment of the invention, there is not necessarily any single embodiment that achieves all of the objects of the invention.

SUMMARY OF THE INVENTION

A visual field testing apparatus in accordance with present invention uses the principle of stereoscopic fixation. The apparatus includes a personal computer for control and administering a visual field examination, one or more high-resolution display members, intelligent software algorithms, and preferably an eye-tracking device. The invention contemplates novel display of the test and fixation targets.

A method for testing the visual field of a patient to determine an extent of at least one scotoma comprises, in accordance with a feature of the present invention, (a) measuring the visual perception of the patient by generating test images at a multiplicity of predetermined points on a visual field display viewed by the patient and recording the patient's responses to the test images to produce a set of raw data, and (b) automatically analyzing the set of raw data to determine a closed curve generally separating points corresponding to unseen test images from other points corresponding to seen test images. The automatic analysis of the raw data includes (c) estimating a size and a shape of an area containing only points corresponding to unseen test images, (d) selecting a series of spaced points along a boundary of said area based on the size and shape estimates, and (e) for each of said spaced points, more precisely determining the boundary of said area by automatically testing additional points located between points corresponding to unseen test images and points corresponding to seen test images.

Pursuant to another feature of the present invention, the more precise determining of the boundary includes selecting at least some of the additional points in dependence on the patient's responses to the testing of others of the additional points. Thus, the present methodology contemplates the selection of test points "on the fly." These test points cannot be known prior to an initial testing of the patient's visual field at a set of predetermined test points. This "on the fly" method improves the accuracy and rapidity of scotoma measurements. The patient is less fatigued and the test results are improved also for that additional reason.

The more precise determining of the boundary includes measuring the visual perception of the patient at the additional points in the patient's visual field by generating respective test images at the additional points on the visual field display and recording the patient's responses to the respective test images to produce additional data pertaining to the visual field of the patient.

The selecting of the additional test points is executed automatically by a programmed computer in accordance with the patient's test responses.

In one specific embodiment of the invention, the spaced points all correspond to test images unseen by the patient and the more precise determining of the boundary includes, for each selected one of the spaced points, (i) selecting a first additional point located between the respective selected spaced point and another tested point located outside the area of unseen test points, (ii) generating a first additional test image at the first additional point, (iii) recording the patient's response to the additional test image, (iv) selecting a second additional point located closer than the first additional point to the area of unseen test points where the additional test image is seen by the patient and farther from the area of unseen test points where the additional test image is unseen by the patient, and (v) continuing to select additional points for testing until two successively tested additional points test differently.

Generally, the spaced points along the curve outlining a detected scotoma are either all outermost unseen test points of the scotoma or innermost seen test points. In the above description, the spaced points along the curve are all unseen test points.

An apparatus for testing the visual field of a patient for scotomas comprises, in accordance with an embodiment of the present invention, two display members located on opposite sides of a plane of symmetry extending through the patient's head, a computer operatively connected to the display members for generating binocularly displaced images of a common fixation object on the display members, and at least two mirrors inclined at different angles with respect to one another for directing light rays from respective ones of the display members to respective ones of the patient's eyes. Each of the mirrors is disposed along an optical axis of a respective eye of the patient, and at least one of the mirrors (for the eye under test) is a beam splitting mirror. A projection screen is located on a side of the beam splitting mirror opposite the patient. A projector is provided for projecting a test image onto the screen. The computer is operatively connected to the projector for controlling the generation of test images on the screen.

The display members are preferably, but not necessarily, LCD display screens.

The display members may substantially face one another, for instance, where the display members are panels located on opposite sides of a sagittal plane through the patient. Such panels may be placed, for instance, outside of the patient's field of vision and outside of the temples.

In accordance with another feature of the present invention, the computer is programmed to generate a series of differentially displaced binocular images of the common object on the display members, so that the object is a three-dimensional moving object.

Pursuant to this feature of the invention, a method for testing the visual field of a patient comprises generating on a test display area a series of test images at different points of the patient's visual field, recording the patient's responses to the test images, and generating, on a pair of spaced display areas during the generating of the test images, two binocularly displaced images of a fixation object so that the fixation object appears to the patient to be three dimensional and in motion.

The fixation object can be virtually anything that is capable of attracting and keeping the patient's attention. Examples of moving fixation objects includes geometric forms and animated figures.

The apparatus of the present invention presents the patient with field test points from a computer-controlled display, and the fixation target is also generated on a computer-controlled display. Pursuant to a particular embodiment of the invention, the fixation object is generated on a different display from the test images. The software presents a predefined set of test points depending on the suspected disease state, and includes an algorithm to trace the perimeter of the suspected scotoma.

A more complete understanding of the present invention, as well as further features and advantages of the invention, will be obtained by reference to the detailed description and drawings.

BRIEF DESCRIPTION OF THE DRAWINGS

FIG. 1B is a 3-dimensional schematic of the stereoscopic visual field examination of FIG. 1A.

FIGS. 3A and 3B show binocularly displaced two-dimensional views of a stereoscopic fixation object utilizable in a visual field testing method in accordance with the present invention.

FIG. 3C is a three-dimensional graphic illustrating fusion of the two images of FIGS. 3A and 3B, showing the resulting 3-dimensional image as it appears to a patient.

FIG. 7A is a schematic perspective view of selected elements of a visual field testing apparatus in accordance with the present invention.

FIG. 7B shows an image of a patient's eye, as output from an eyetracking CCD camera shown in FIG. 7A.

FIG. 7C is a schematic perspective view of additional selected elements of the visual field testing apparatus of FIG. 7A, showing infrared LED's for illuminating the patient's pupil and iris.

DETAILED DESCRIPTION OF THE PREFERRED EMBODIMENT OF THE INVENTION

The invention will now be described in more detail by way of example with reference to the embodiments shown in the accompanying figures. It should be kept in mind that the following described embodiment in only presented by way of example and should not be construed as limiting the inventive concept to any particular physical configuration.

Figure 1A:
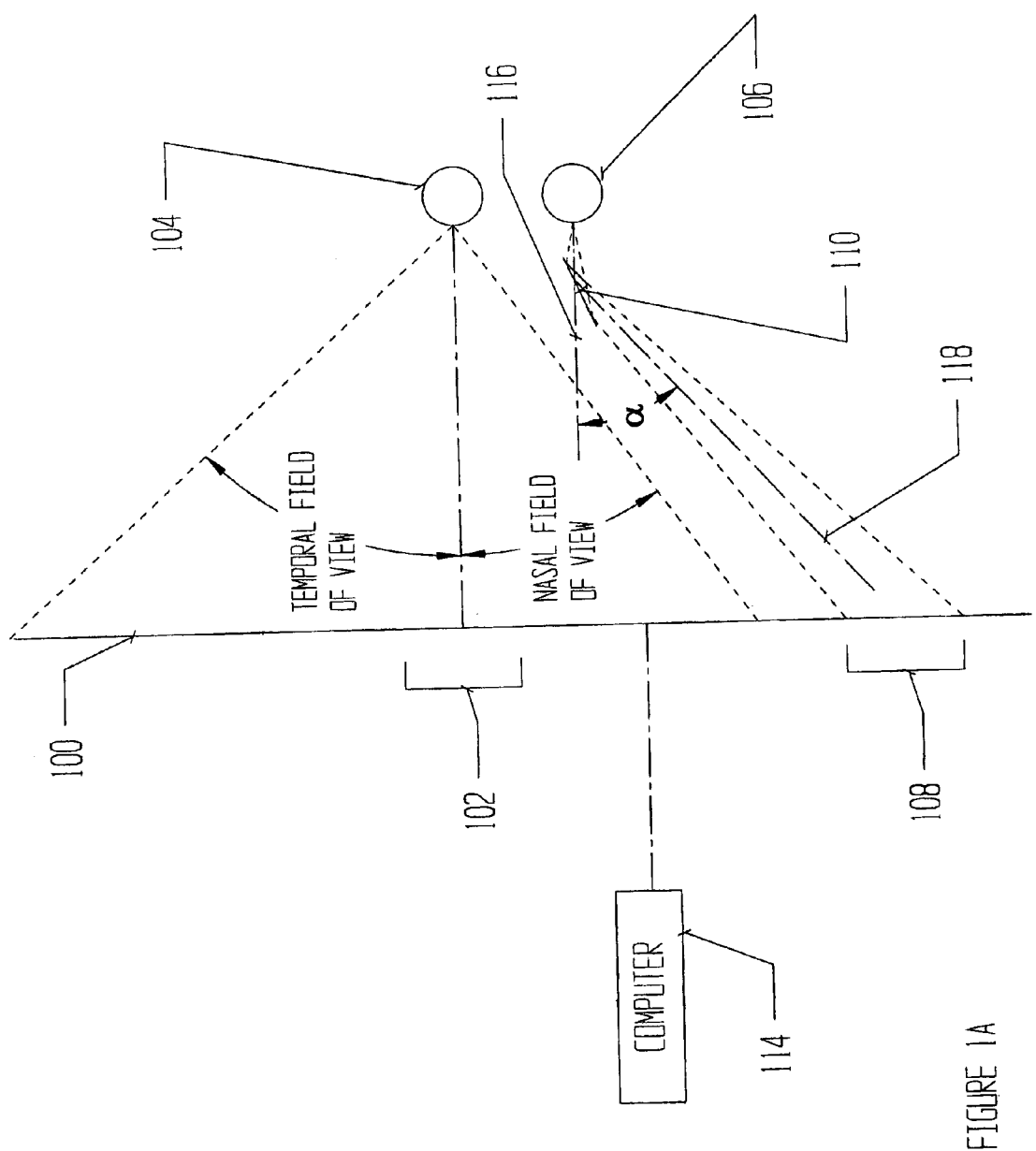
FIG. 1A is a 2-dimensional schematic of a stereoscopic visual field examination that incorporates a computer display, in accordance with the present invention.

A preferred embodiment of the present invention is depicted cross section in FIG. 1A and three-dimensionally in FIG. 1B. A computer display 100 is used to present a patient with a graphical fixation area 102, and flashing test points 112 throughout the central visual field (for example 30 degrees nasally and 50 degrees temporally) to the eye under test 104. The technique described herein could certainly be extended to include the entire field of view of the eye as perimeters do, but will be described here only in the campimeter form. The computer display also serves to present to the eye not under test 106, a fixation area 108 that fuses stereoscopically with the other fixation area 102. Both fixation areas 102 & 108 are nearly identical imagery with on notable difference, namely the images are binocularly displaced images, from different perspectives. Since only one eye 104 is to be under test at a time, and only this eye is to see the test points, rather than occlude the eye not under test 106 (as with commercial perimeters) the latter's view is redirected to fixation area 108, which is located on another portion of the computer display 100, by placing a first surface mirror 110 at an appropriate angle. This eye 106 therefore views its own fixation area 108 and nothing else.

Figure 2:
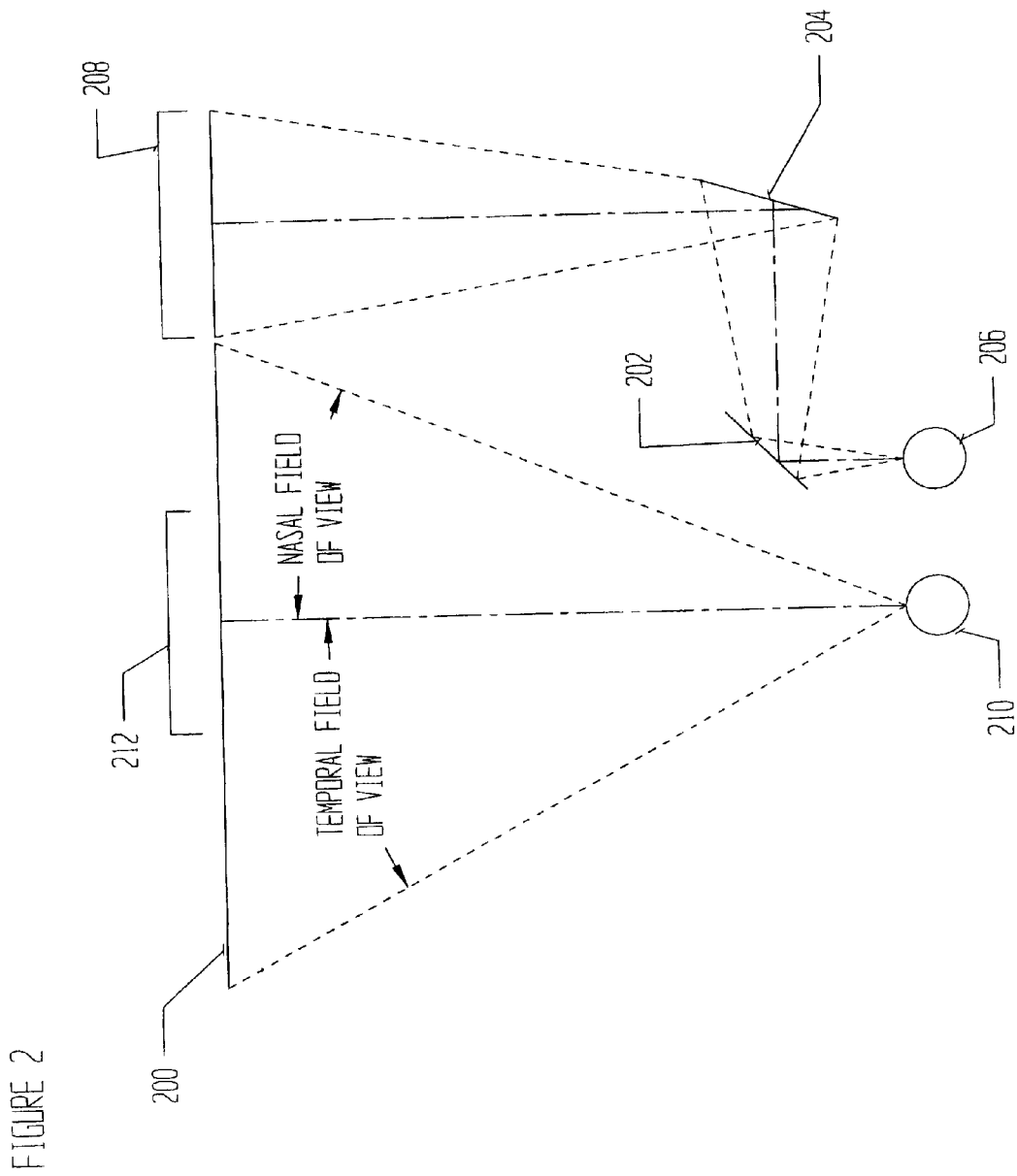
FIG. 2 is a diagram of an alternative arrangement for a stereoscopic visual field examination.

An alternative design for the patient to view two fixation areas is shown in FIG. 2. Here two first surface mirrors 202 & 204 are situated before the eye not under test 206 and positioned at appropriate angles to view a fixation area 208. The eye under test 210 views a computer display 200 and a fixation area 212 directly as in the arrangement of FIG. 1.

A visual-field test using the arrangement of FIGS. 1A, 1B or 2 is generally performed at near reading distance though this distance can be varied. It should be noted that for system shown in FIGS. 1A and 1B, the distance from each fixation area to its respective eye will be different due to the different view angles, and the fixation area 108 for the eye not under test 106 will appear smaller since it is further away. This discrepancy in apparent size must be compensated since each fixation area must appear identical to the patient. To remedy the discrepancy, a computer 114 operatively connected to display 100 can draw this fixation area 108 on the display slightly larger than the fixation area 102 by scaling fixation area 108 by the sine of the angle α between an optic axis 116 of the eye not under test 106 and a sight path 118. This fixation area will also be distorted due to the angular projection, which will also need to be compensated by the computer 114 by drawing the fixation area with negative distortion. In the system shown in FIG. 2, the fixation area 208 will also appear smaller since it is further away due to the extra path length caused by the two mirrors 202 and 204, which is essentially the distance between the two mirrors. This fixation area 208, however, will not be distorted since the unfolded path through the mirrors 202 and 204 is a straight line perpendicular to the display 200.

Once the two fixation areas 102, 108 or 212, 208 are presented to each eye 104, 106 or 210, 206, stereoscopic compulsion forces the images to merge, and the fixation areas 102, 108 or 212, 208 appear to the patient as one image. Images now drawn on the display will appear three-dimensional, provided the two images are taken from different perspectives. The method of presenting each eye an image taken from a different perspective so that it appears three-dimensional is the basis of a stereoscope, and is well known. If the fixation area is a simple geometric figure such as an annular ring, and if the ring from each respective image is offset slightly in opposite directions, the ring will appear to the patient as floating in front or behind the display depending on the relative direction of the offset. For ease of fusion, and for the emmetropic eye, a positive lens is placed before each eye, which magnifies each image to aid in their overlap. These lenses are configured such that the fixation image is at the focal length of the lens thereby producing a magnified image located at infinity. By locating the image at infinity, the patient's accommodation is relaxed and fusion happens with little concentration required of the patient. The ease of fusion occurs since the angle of convergence of the two eyes is reduced when images are at infinity rather than up close. If the patients' vision needs correction, additional standard ophthalmic test lenses can be added, or they can wear their prescribed corrective lenses during the test. A fixation area that appears three-dimensional when fused, stays fused more easily than two two-dimensional images.

Once the eyes 104, 106 or 210, 206 are fixated, the mapping of the visual field consists of flashing test images at generally randomly selected points 112 (FIG. 2) from among a set of predetermined points throughout the visual field in the area of interest. The test is subjective, and the patient must indicate when a test flash was seen. All seen and unseen test points are recorded by the computer 114 (FIG. 1A), and at the end of the test the computer presents these points as a map of the field in user selectable display. The seen and unseen points represent the visual field of the patient and are a projection of the active and inactive portions of the retina through the eye 104, 106 or 210, 206.

Fixation areas 102, 108 or 212, 208 can take several forms, the simplest would be a small circle (1-2 degrees of the field of vision in extent) situated in the center of vision. This circle, when fused stereoscopically, appears to be floating in front of the computer display 100, 200. For the circle to have this appearance of depth, one image is offset (binocularly displaced) with respect to the other by a small amount, mimicking the effect of different perspectives. The distance by which the two images are separated is related to the apparent distance the circle will be floating in front of the display 100, 200. Fixation areas 102, 108 or 212, 208 can also add value to the test, as a combination of geometrical shapes in different colors is useful in ascertaining what is visible to a diseased patient. Since the test is subjective, it requires the patient to be cooperative and attentive during the test, and a combination of geometrical figures can help ascertain the level of cooperation of the patient from feedback from what they see. One example of a pair of binocularly displaced geometrical fixation areas 301, 302 is shown in FIGS. 3A and 3B, which consists of easily identifiable simple shapes that appear as a red pyramid 304 with a green disk 306 at the apex, and a large blue circle 308 in a plane apparently located behind the base of the pyramid, when the fixation images or areas 301 and 302 are optically fused by the patient (FIG. 3C). To achieve this three-dimensional effect, each image 301, 302 presented the respective eye is skewed slightly or offset from the relative center, to mimic the effect of different perspectives. The fixation image 301 presented to the left eye is skewed to the right, and the fixation image 302 presented to the right eye is skewed to the left, and the resulting image 303 (FIG. 3C) appears three-dimensional.

The advantage to stereoscopic fixation in testing the visual field over monocular visual field instruments is that if the patient has a central scotoma in the eye under test and cannot see the central fixation point and the eye not under test is free from central defects, when the brain fuses the two images it 'fills in' the missing portion. To the patient therefore, the fixation image appears to be a single image with no missing features. Whether the image appears stereoscopic with the appearance of depth depends on how much of the remaining fixation image is seen by the scotomatous eye. The size of the fixation imagery used is relatively large, covering approximately 20 degrees of the field of vision with a center fixation point. If the scotoma for the eye under test extends only over a portion of the fixation image, say 5 degrees over the center, and the patient can see the remaining fixation image, it is likely the patient will sense that the entire image has depth. By maintaining peripheral fusion, fixation is maintained and the test can be carried out and central scotomas can be mapped. The eye not under test thus views its own fixation area for the duration of the test and maintains fixation while test points are presented to the other eye.

There are many instances where patients tested on the campimeter will have a central scotoma in both eyes, as well as patients with age-related macular degeneration, or other retinal diseases that cause a large scotoma, some out to 40-60 degrees. One would think that in these cases that the present device would suffer the same problems as monocular perimetry. However, if a bright enough stimulus is presented to these patients, they would be able to "see through" a relative or absolute scotoma which would achieve steady fixation, because a true absolute scotoma is rare. Most defects are found to have some level of faint sensitivity. The addition of a small very bright light located in the center of the fixation area for the eye not under test will keep fixation steady and the field can be measured. Additionally, fixation can be aided by means of peripheral fusion of patterns in the fixation area surrounding (+/−20 degrees) the central fixation point as in the case where one eye has a central scotoma.

Since the fixation area or image 102, 108 or 212, 208 is drawn by the computer (e.g., 114), the fixation area or image need not be a static image, but could be animated to further increase attention from the patient. For example, an animated target could be a sphere that appears to be rotating on an axis. Any other conceivable figure could be made dynamic and appear three-dimensional. Examples include geometrical fixation images as discussed above with reference to FIGS. 3A-3C, or a graphical or cartoon representation.

One critical aspect of the fixation areas 102, 108 or 212, 208 is that they be aligned with each other and with the patient's eyes. The center of each fixation area 102, 108 or 212, 208 should be coincident with the respective axis of the patient's eyes. This would require an up/down left/right adjustability of the fixation areas 102, 108 or 212, 208. The computer 114 can draw the fixation areas 102, 108 or 212, 208 anywhere they need to be to facilitate alignment of the two images. An alignment procedure is performed prior to any testing, and the computer will save this alignment data for that particular patient.

Figure 6:
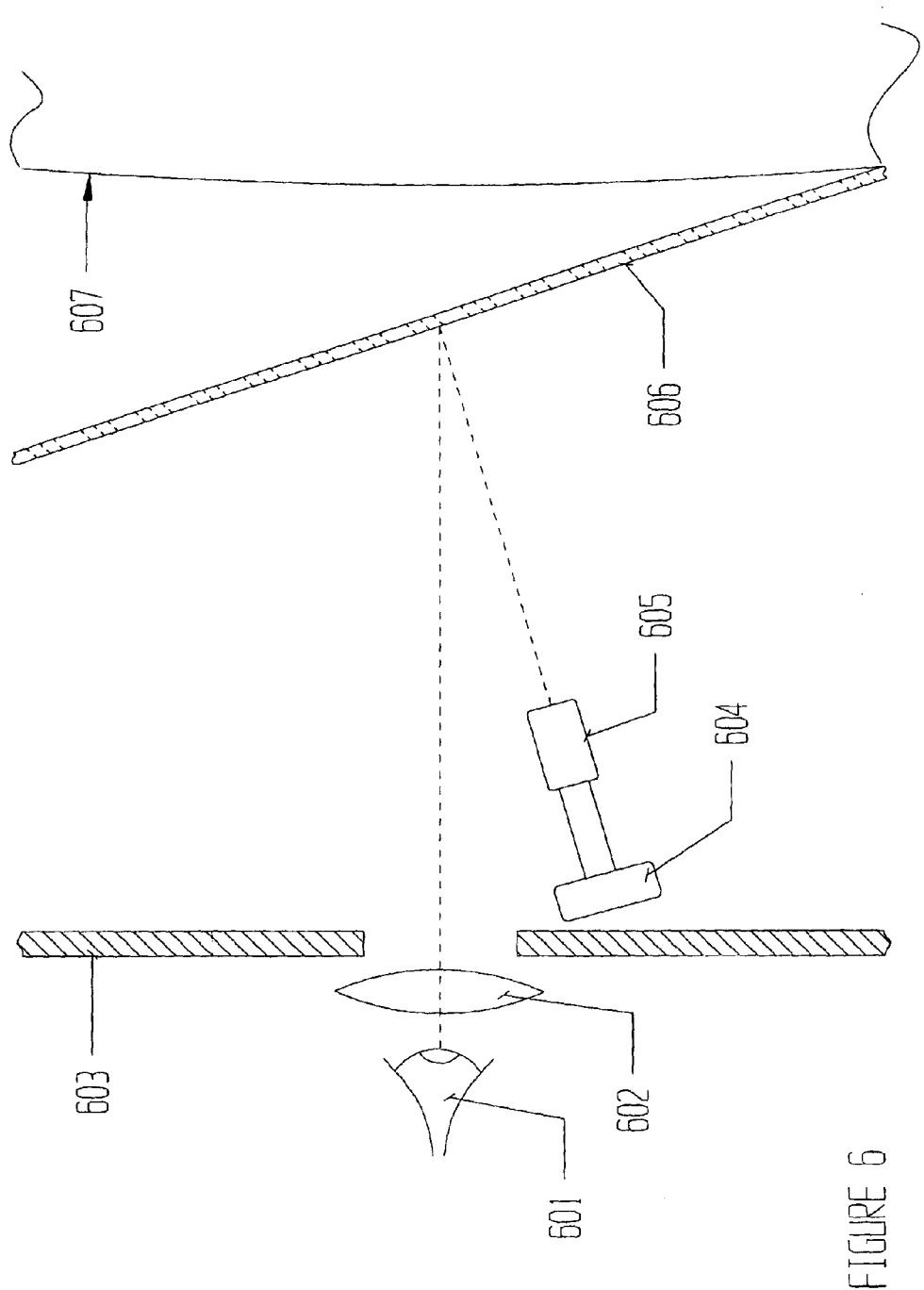
FIG. 6 is a diagrammatic side-view of an eyetracker system employed in a visual field testing apparatus in accordance with the present invention.

During a test and while fusion of the two fixation areas is maintained, the patient is to look at the fixation areas 102, 108 or 212, 208 only, and test images exemplarily in the form of bright dots are flashed throughout the field at predetermined test points selected by the computer (114). The eye not under test 106, 206 does not view any of the flashed test images, but continues to fixate on its own fixation area 108, 208 to hold the eye under test 104,210 fixated as well. The patient indicates that he or she has seen any particular test image by pressing a button wired to the computer. Since the eye 104, 106, 206, 210 must be fixated to make the test point valid (per the definition of visual field), if the patient looks directly at the flashed dot, the point should be disregarded as a seen point. The patient may be unaware, fatigued, distracted, or careless, and look at the flash directly; therefore to achieve accurate results the movement of the eye must be monitored, and an eye-tracker as discussed below with reference to FIG. 6 is incorporated into the system. Eyetracking devices are well known and typically use a low power infrared light (i.e. infrared light emitting diode), optics, and a detector. Incorporated into most automatic perimeters, these systems detect any shift in the patient's gaze from the central fixation point during a visual field examination.

Figure 4A:
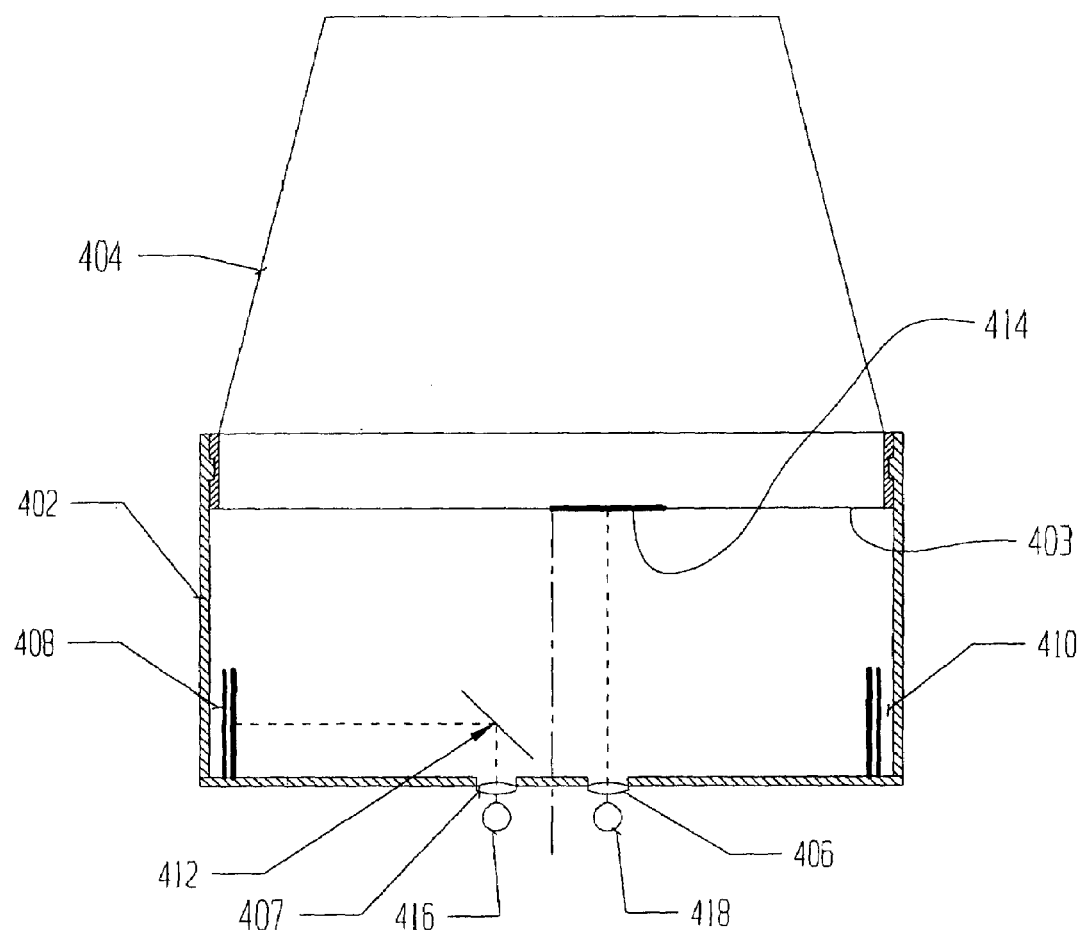
FIG. 4A is a schematic cross-sectional view of display elements of a visual field testing apparatus in accordance with the present invention, particularly a CRT and printed secondary fixation areas or display panels.
Figure 4B:
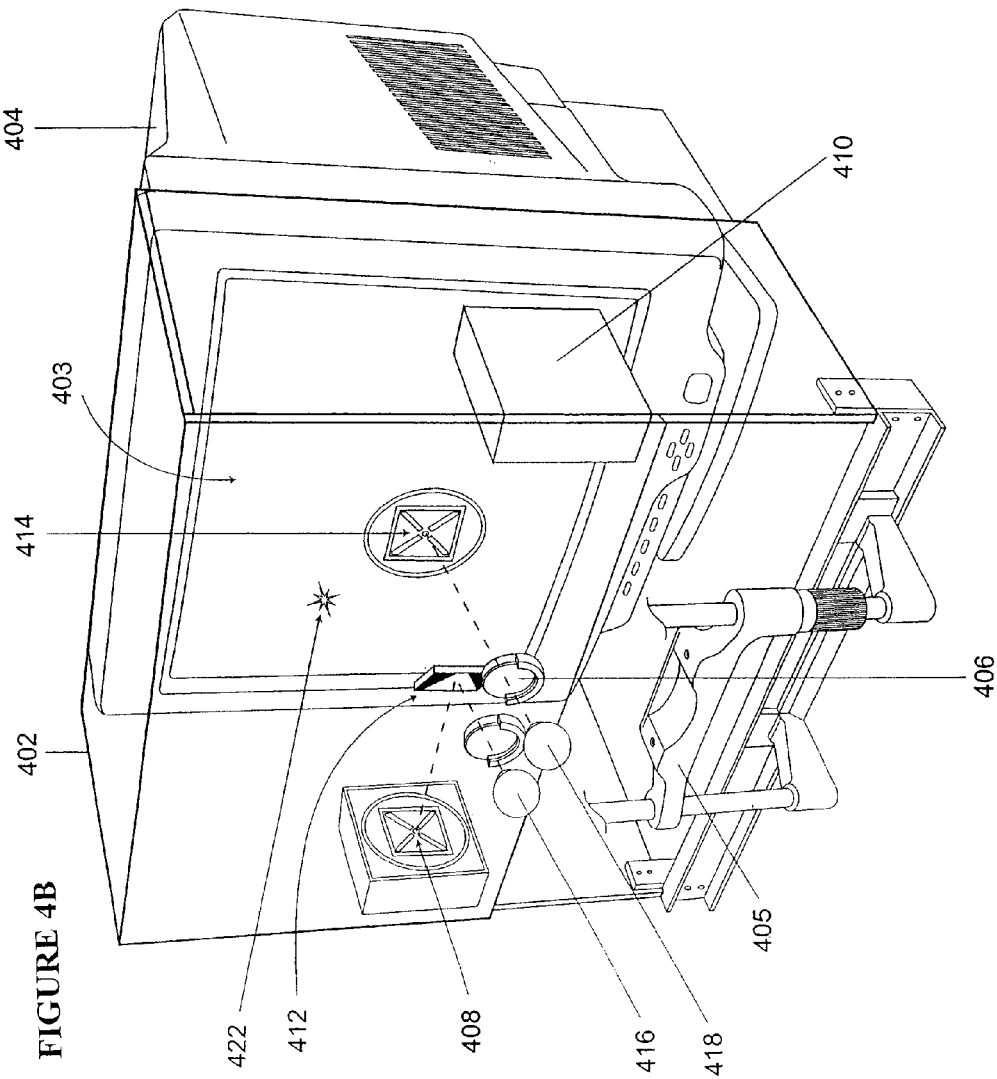
FIG. 4B is a schematic three-dimensional view of display elements of a visual field testing apparatus in accordance with the present invention, similar to elements shown in FIG. 4A.

As disclosed herein, several options are available for a computer-controlled display for presenting fixation areas 102, 108 or 212, 208 and test images 112. A cathode ray tube (CRT) can be used as the display 100 or 200 provided the CRT has the necessary viewable area to display both the testing arena and the fixation area for the eye not under test. Presently, readily available CRT's for computers range from 15" to 21" (diagonal and not actual viewing area), which would be sufficient if the fixation area 102, 108 or 212, 208 were small. Readily available liquid crystal display (LCD) monitors can also be used. Displays that are discrete systems (not part of a laptop) more typically range from 15" to 17", have larger viewable areas, and are available with wide screens (16:9 aspect ratio) up to 24", but to date, are prohibitively expensive. Other display types are available and could be used that have large viewing areas for instance plasma displays but are also very expensive. If one of these readily available monitors is used, and if the screen area is not enough to perform the full test, the fixation area particularly for the eye not under test could be located not on the screen but elsewhere. In this case the fixation image for the eye not under test would need to be an exact replication of the screen image both in graphical imagery and brightness. In a prototype instrument that was built, this was done by printing an exact replica of the central fixation area that was displayed on the computer display onto transparent film, and then backlighting the film so that the intensity was nearly identical with that of the computer display. This prototype is shown in cross-section in FIG. 4A and three-dimensionally in FIG. 4B, where a rectangular box 402 exemplarily made of acrylic sheets is attached to a CRT 404 and extends outward toward the patient.

The depth of the box 402 (FIGS. 4A and 4B) defines the distance of the patient's eye under test 418 to the image on a screen 403 of CRT 404, which also defines the angle of visual field that will be subtended by the eye under test. The instrument also includes a standard ophthalmic chin/forehead rest 405 to keep the patient's head steady during a test. Two holes 407 are cut in the box 402, which are the ports through which the patient will view the images. These ports 407 hold magnifying lenses 406 as well as standard ophthalmic test lenses for vision correction if necessary. Printed fixation areas or images 408 and 410 are disposed at each side of the box 402 for alternatively testing the left and right eye. Each printed fixation area or image 408 and 410 is held in a mount that is adjustable along the two axes perpendicular to the optical axis of the eye under test to facilitate alignment. The print of the fixation area or image 408, 410 is backlit with a compact source of light, for example an electro-luminescent panel. The printed fixation areas 408, 410 must have the same brightness (so the images appear identical) as a fixation area 414 displayed on the computer screen 403, so the luminance of printed fixation areas or images 408, 410 can be matched to that of the screen 403. This is done by adjusting the color on the screen 403 in software to match the backlighting source. For the eye not under test 416 to view its respective printed fixation area or image 408, a first surface mirror 412 is mounted at 45 degrees in front of the eye. The mirror 412 has an angular adjustment of +/−5 degrees to facilitate alignment and to adjust for different inter-pupillary distances, and is contained in a separate or dedicated housing (not shown) making up an assembly that contains the mirror and a pivoting mechanism. The mirror assembly (mirror and pivoting mechanism) is required to change positions—that is, being situated in front of the left eye or the right eye depending on which eye is under test. This is accomplished by rotating the mirror assembly about a fixed point so that the mirror 412 falls into position in front of the other eye. In order for the image to appear square, the mirror surface needs to be masked with black paint to eliminate the angular projection that would occur with a rectangular mirror. The eye under test 418 views the CRT screen 403 directly.

Figure 5:
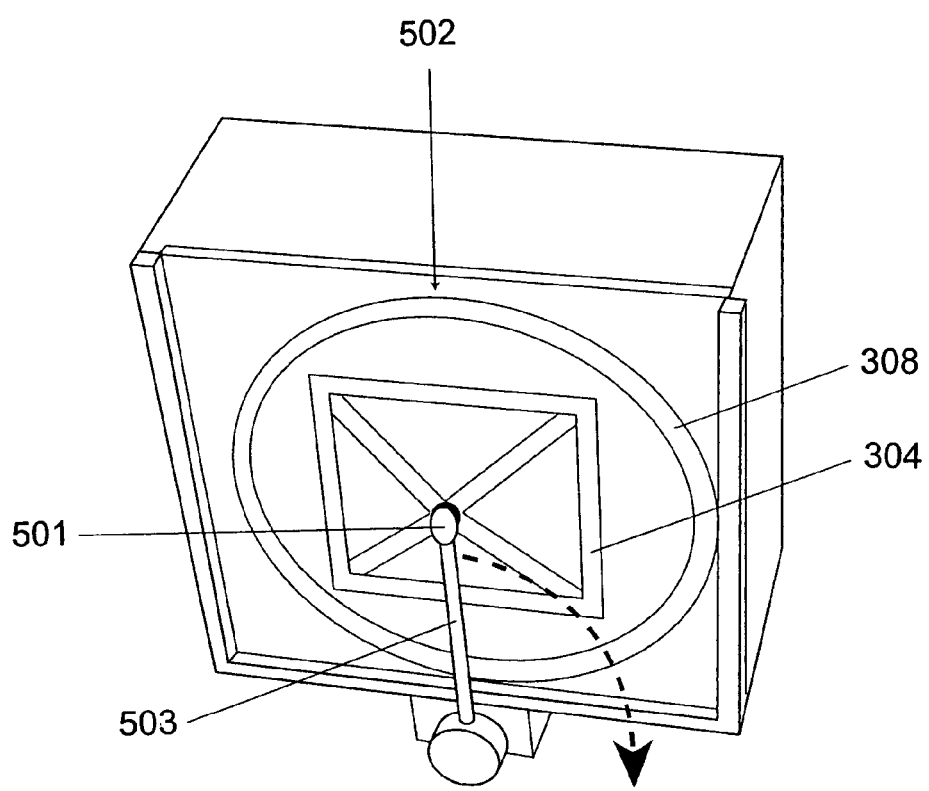
FIG. 5 is a perspective view of a fixation display panel utilizable in the apparatus of FIGS. 4A and 4B, showing a bright light element utilizable with the fixation display panel for measurement of the visual field when the patient has centrally located defects in both eyes or poor visual acuity.

FIG. 5 shows a 3 mm diameter Light Emitting Diode (LED) 501 with prime emission in the green portion of the electromagnetic spectrum for testing patients with central scotomas in both eyes. Diode 501 is mounted on or disposed in front of a secondary fixation image 502, to be viewed by the eye not under test, on the end of a wand 503 that may be adjusted and aligned so that the diode 501 is exactly in the center of the field. (Secondary fixation image 502 may be the geometrical form discussed above with reference to FIGS. 3A-3C.) The wand 503 and the LED 501 have the ability to flip out of the way when not needed. Currently available LEDs 501 have the ability to produce remarkable levels of brightness, 7.8 Candelas within a 15-degree emission angle. A handheld control unit (not shown) may be provided to turn on the LED 501 when needed, with a switch (not shown) to change between right eye and left eye, an adjustment (not shown) for the intensity, and the ability to flash the LED via a pushbutton switch (not shown) to get the attention of the patient.

As illustrated in FIG. 6, the hardware portion of the eyetracker consists of a charge-coupled device (CCD) camera 604 that outputs standard video (NTSC). For image-processing reasons, it is desired to have the image of the eye fill the whole frame of video (see FIG. 7B). This is accomplished by selecting an appropriate imaging lens (not shown) and disposing the lens in a custom lens barrel 605. When the output of the camera 604 is observed on a video monitor (e.g., monitor 705 in FIG. 7B), the edges of the sclera 710 are seen at the edges of the monitor with the iris 712 and the pupil 714 visible near the center. It is desirable to have the camera 604 for the eyetracker off-axis, that is, out of view of the patient so none of the field that being tested is obstructed. A conventional manner to achieve an off axis camera, is to mount a beamsplitter ('two-way mirror') at 45 degrees to the eye under test 601 (FIG. 6). This is impractical in this configuration. Since the patient sees such a wide field of view, the beamsplitter, so not to be apparent to the patient, must be cumbersomely large. A large beamsplitter (usually a piece of flat glass with a partially reflecting coating) is difficult to mount, let alone shift in front of the other eye for testing. It has been observed that since the patient is staring at a computer display 607, an image of his or her eye is formed in the display, reflected from the glass surface of the computer monitor or CRT display, exactly as a virtual image is formed in a curved mirror. The camera 604 then could be mounted above the eye ports, pointing at the virtual image formed in the display. In practice it has been determined that the actual surface of the display 607 cannot be used since most computer monitors have an antireflection or antiglare coating applied to their screen surfaces. However, a flat sheet of clear acrylic 606 may be inserted inside the bounds of the stereocampimeter box or enclosure 603, with this sheet reflecting an image of the eye to the eyetracking camera 604. The acrylic sheet 606 may be tilted (perpendicular to the patient's line of sight) which reduces the necessary tilt of the camera 604, hence reducing distortion of the image. Acrylic beamsplitter 606 may be replaced with an infrared/visible transmitting mirror (known as "hot mirror") to boost the reflectivity of the image of the eye.

For the camera 604 to see an image of the eye, the eye must be illuminated, and this illumination should not distract the patient. Preferably, the eye is side-illuminated with infrared light emitting diodes as illustrated at 706 in FIG. 7C, and a visible blocking/infrared transmitting filter ('long-pass filter') (not shown) is inserted into the lens barrel 605. Accordingly, the camera 604 detects only infrared radiation above 860 nanometers, outside the visible spectrum.

As depicted in FIG. 7C, light emitting diodes 705 are low power diodes mounted near eye port lenses 707 (FIG. 7C) at a steep angle (approximately 80 degrees) to the axis of the eye. This ensures even illumination of the eye, and avoids any significant amount of infrared light entering the patient's pupil. What is seen then in a video monitor 705 (FIG. 7B) of the illuminated eye is a bright sclera 710 and iris 712 (the iris is highly reflective to red and infrared light), and a dark, almost black pupil 714. A camera 702 (or 604) must be positionable in front of whichever eye is under test in an examination, and is therefore mounted on a rail system 701 (FIG. 7A) that accurately positions the camera in front of the left or right eye. The mechanical system that holds the camera 604 or 702 also allows for precise alignment of the camera in two linear dimensions as well as an angular adjustment.

A schematic side view of an eyetracking system is shown in FIG. 6, showing the eye under test 601, a stereoscope magnifying lens 602, a section of the housing or enclosure 603, CCD camera 604 and lens/filter assembly 605, acrylic beamsplitter 606 and a section of the CRT 607. FIG. 7A shows the inner workings of a similarly configured eyetracking system including camera sliding rail 701, CCD camera 702 and lens barrel 716. A 45-degree mirror assembly 703, and a printed fixation image or LCD display 704 are also in view. FIG. 7B shows the image of the eye captured by the CCD camera 702 as seen on the video monitor 705. FIG. 7C shows the infrared LED's 706 illuminating the eye, as well as the magnifying lenses 707 of the stereoscope and a forehead rest 708.

Now that the camera 604 or 702 has an image of the patient's eye under test, the output of the camera is fed into the computer (e.g., 114) for analysis. The video signal from the camera 604 or 702 is input into a data acquisition board or frame grabber (not illustrated), mounted in the computer (plugs into computer's motherboard). The computer is provided with separate eyetracking software that is continually running in the background during a visual field test and sends a signal to the main program, which is flashing and recording test points. The signal to the main program is a yes or no answer as to whether the patient moved his or her eye during the test, or was fixating. If the software finds that the eye moved from the center fixation point, and the patient presses the button, the main program discards this point as being seen (since it is invalid) and tags it for retesting later. The algorithms that determine the coordinates of the center of the pupil given the raw picture of the eye are described with the other features of the software.

The software that monitors eye position does so by an algorithm that finds the center of the pupil during testing and compares that real-time location of the pupil's center to the location determined prior to the start of testing. A baseline image is taken and sent to the computer, which locates the edge and the center of the pupil. During testing, additional images are collected and compared to the baseline image in real time (30 frames per second), to insure that the eye remains properly fixated while each test point is flashed Having an image of the eye provides an additional advantage during alignment procedures. Once the camera 604 or 702 has been correctly aligned to the housing or enclosure 603, 718 of the campimeter, the image of the patient's eye from the camera can be used to ensure correct positioning of the patient's eyes with respect to the apparatus as well. The eyetracker system (including the camera 604, 702 and the associated software) can report the distance the eye is off-center, for more accurate positioning than the operator could achieve by looking at the monitor alone. The patient is situated in the device using a standard chin/forehead rest 406, 708.

It is convenient to have an additional computer display for the operator to monitor the test. Any type of standard monitor may be used. By using a video card in the computer that accepts two video displays, the operator can see the exact image being displayed to the patient. The additional monitor is also useful for the operator to set the test parameters before the test, and to know when the test is complete.

CRT, liquid crystal (LCD), and plasma displays are all viable options. However, rather than being limited to commercially available screen sizes, a visual-field testing apparatus may utilize a video display projector to achieve any size computer display within a range. Projection of video (computer or TV) is well known, and the most recent methods are usually achieved with a relatively small, high resolution LCD panel (~5") which is back lit with a white light source, and projection optics transfer and enlarge the LCD panel to an image formed on a screen. The device functions almost identically to a conventional photographic slide projector, with the slide being replaced by the LCD panel.

Figure 8:
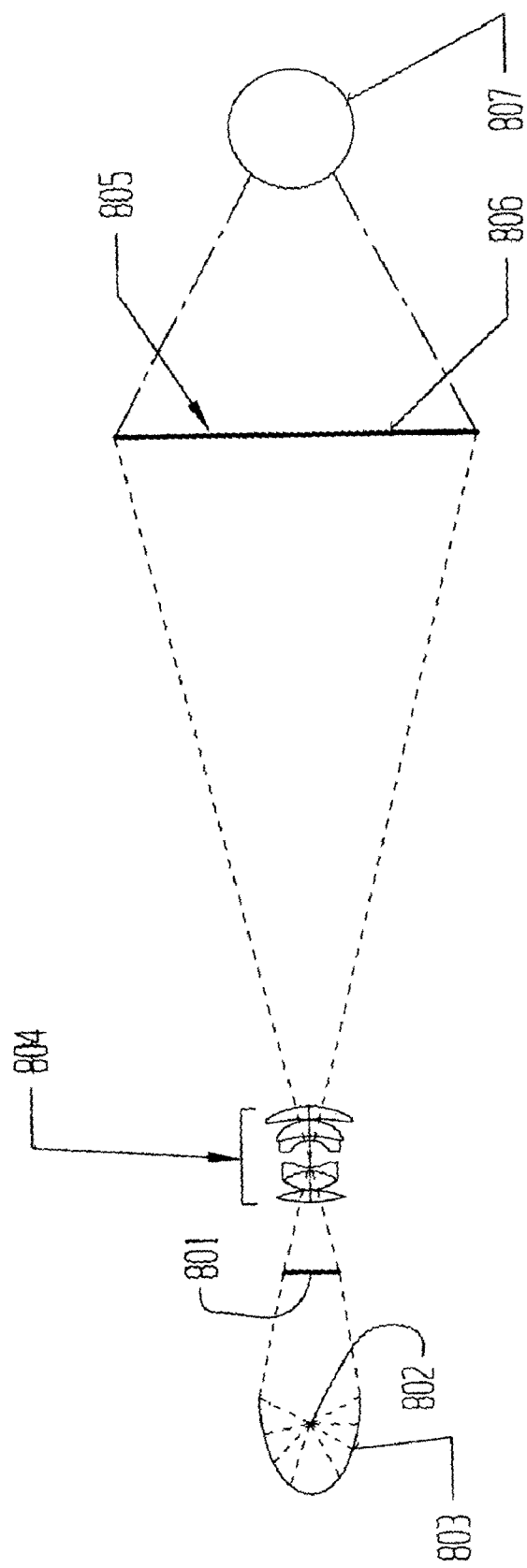
FIG. 8 is a diagram depicting a rear projection LCD video projection system of a visual field testing apparatus in accordance with the present invention.

Referring to FIG. 8, which is a cross sectional representation of the video projection system, an LCD panel 801 is backlit with a white light source 802 such as a filament or arc lamp, surrounded by a reflector 803 to act as a condenser. A projection lens 804 produces an image 805 of the LCD on a translucent screen 806 such as ground glass or diffuse plastic. An observer 807 can view this screen from the opposite side, so the projector is being used in the 'rear projection' mode.

Instead of a flat projection screen for the campimeter, a curved projection screen can be used whose radius is concentric with the approximate radius of the eyeball, thereby removing the non-linear effects of projecting a three-dimensional surface (the retina) onto a two-dimensional surface (video monitor). This also serves to compact the instrument even more since the diameter of a spherical shell is less than a flat screen having the same surface area. The design of the projection lens in the case of a curved screen introduces significant field curvature (or equal to that of the curvature of the screen) of the image, so that at every point on the spherical shell, the image is in focus. It is not to be overlooked, however, that this method will produce an image of diminishing brightness toward the edges of the sphere, proportional to the cosine of the incident angle. Since the intensity of the image is expected to be high (commercially available video projectors are meant to be used with large image sizes in reflection mode) due to relative small image size and rear projection mode of operation, a physical or digital filter can be applied to even out the intensity across the spherical surface.

Figure 9:
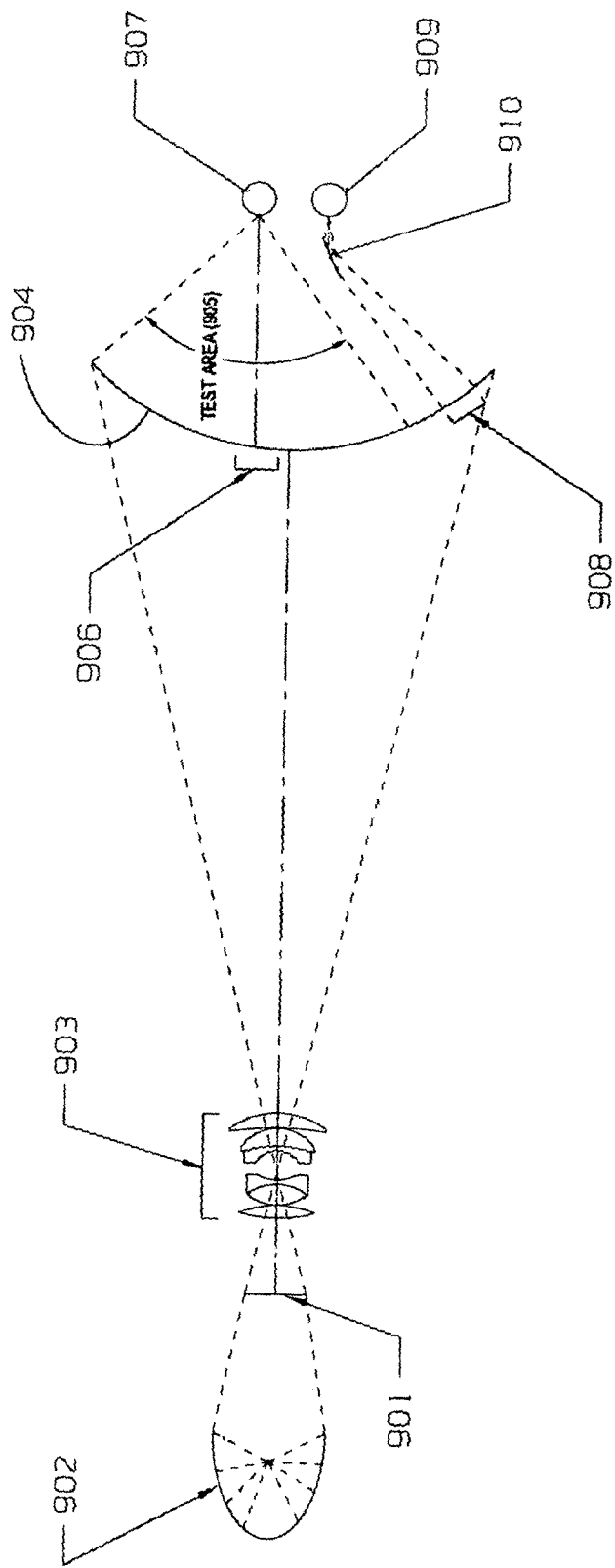
FIG. 9 is a diagram depicting an LCD projection system in a rear-projection mode using a curved screen to display test and fixation areas, in accordance with the present invention.

Referring to FIG. 9, an LCD panel 901 is again backlit with a white light source surrounded by a reflector 902. A projection lens 903 with negative field curvature produces an enlarged image of the LCD panel on a spherical screen 904, which is translucent. Using this arrangement, a test area 905 and a primary fixation 906 area can be displayed on the majority of the curved screen, and an eye under test 907 can view the test area and the primary fixation area directly. A secondary fixation image 908 for an eye not under test 909 is projected onto the remaining portion of the display, and viewed via an angled mirror 910 placed before the eye not under test 909. Note that there is an additional advantage in using the curved screen, in that the secondary fixation image 908 will not be distorted and is equally distant from the eye not under test 909 as the primary fixation image 906 is from the eye under test 907. Displaying both fixation images on a flat screen would require the secondary fixation image to be drawn with 'negative' distortion to make it appear straight due to the projection, and would need to be larger, since it would effectively be further away (by sine of the angle), to appear identical in size to the primary fixation image.

Using a curved projection screen with a video projector emanating from the rear of the screen solves many of the problems of the CRT based instrument, namely the size and weight limitations on screen size, and cost. Of course a curved projection screen introduces other design challenges to implement the desired features of the device. For instance, the addition of a small bright light on the secondary fixation target aids in the fixation by a patient with low vision or poor visual acuity. Since it is not practical to add a light emitting diode to the fixation area which in the projection system would be drawn on a translucent screen, this bright light is projected from a laser diode onto the projection screen. This is done in one of two ways—either projected onto the screen and the point of light is viewed in reflection mode, or mounted in the vicinity of the video projector and used in transmissive mode. In either case, the position of the beam can be changed by moveable mirrors forming a two-dimensional scanner. The scanner can be a simple arrangement whereby two mirrors are mounted to motorized rotation stages that have the ability to steer the beam to the desired location with a high degree of position accuracy. Computer control of motors is a relatively simple task, with commercial systems available at a relatively low cost including high-resolution motors and computer interface boards. With the ability to place a focused spot anywhere on the projection screen, it may also be useful at times to project this spot in the center of the fixation area for the eye under test, in cases where this eye is severely degraded in visual acuity or has low vision. It will also be possible to vary the size of the projected spot if the focusing lens is movable, i.e. on a motorized stage controlled by the computer. The computer can also control turning the laser on when desired and could also pulse, as well as varying the intensity.

Figure 10:
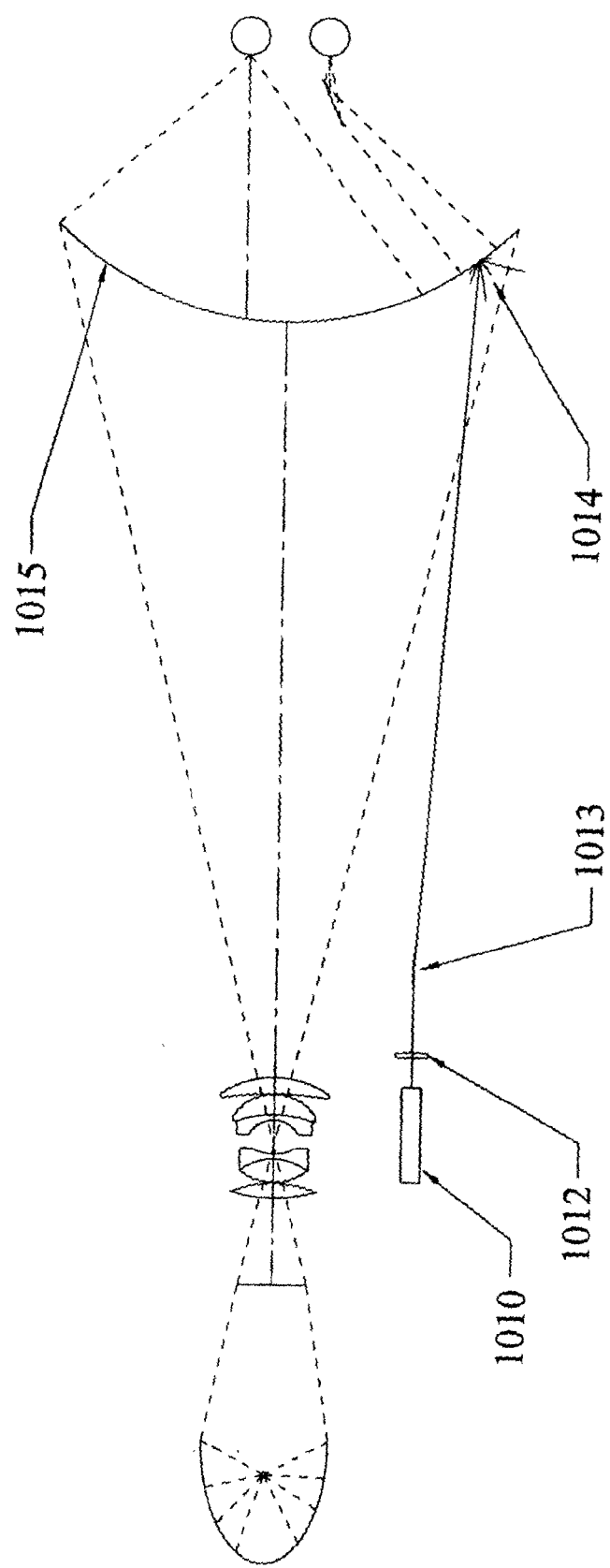
FIG. 10 is a diagram depicting the use, pursuant to the present invention, of a movable laser spot to produce a bright light in a rear-projection mode LCD projection system for measurement of the visual field when the patient has centrally located defects in both eyes or poor visual acuity.

The transmissive mode discussed above is shown in FIG. 10 wherein a rear projection system includes a laser 1010, a focusing lens 1012, and a scan mirror 1013, for generating a diffuse bright spot 1014 on a curved screen 1015. Other elements of the projection system of FIG. 10 are discussed above with reference to FIG. 9.

Campimetric video projection systems as discussed hereinabove with reference to FIGS. 8-10 also require an eyetracker. The projection systems may use a more conventional eyetracker that would monitor the eye directly through a small beamsplitter (not shown) located behind the projection screen. The algorithms used in a CRT based system to find the position of the pupil could be used in the projection type system.

It is also convenient to have an additional computer display for the operator to monitor what is happening during the test. Any type of standard monitor could be used, and it would display the exact image being displayed to the patient. The additional monitor is also useful for the operator to set the test parameters before the test, and an indication when the test is complete.

An alternative to video projection of the testing arena and fixation images has been constructed where fixation images lie outside the testing area, as discussed above with reference to FIGS. 4A and 4B. In this configuration, the system incorporates two small LCD panels (for instance Caltron Industries 6.4" VGA TFT LCD Monitors) capable of displaying video imagery. The LCD panels display computer-generated binocularly displaced fixation images (static or dynamic) such that the resulting image as perceived by the patient is stereoscopically fused as described above. The patient's eyes view their respective fixation images by way of two mirrors placed before the eyes, the mirrors each being inclined at 45 degrees to the optical axis of the respective eye.

Figure 19:
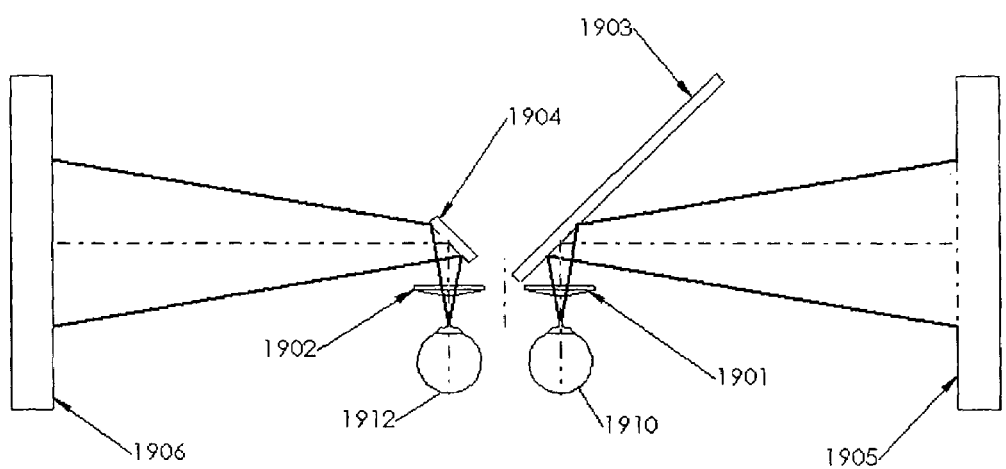
FIG. 19 is a schematic plan view depicting optical elements of a visual field testing apparatus in accordance with another embodiment of the present invention.

Referring to FIG. 19, each eye 1910, 1912 views a separate LCD panel 1905, 1906 through a respective stereoscope lens 1901, 1902 the purpose of which is described above, with a mirror 1903 in front of the left eye 1910 inclined at −45 degrees and a mirror 1904 in front of the right eye 1912 inclined at +45 degrees X04. The LCD panels 1905, 1906 are equidistant and perpendicular to the axis of each eye, and each displays fixation imagery such that three-dimensionality is achieved.

Since in this configuration, the LCDs display only fixation imagery for each respective eye 1910, 1912, in order to carry out a campimetric examination, an area for flashing test points must be incorporated in the system. This is done in practice by making the mirror 1903 or 1904 for the eye under test partially reflecting 'a beamsplitter', so that the eye 1910 or 1912 can see the respective LCD 1905 or 1906, as well as seeing a testing area in front of the eye.

Figure 20:
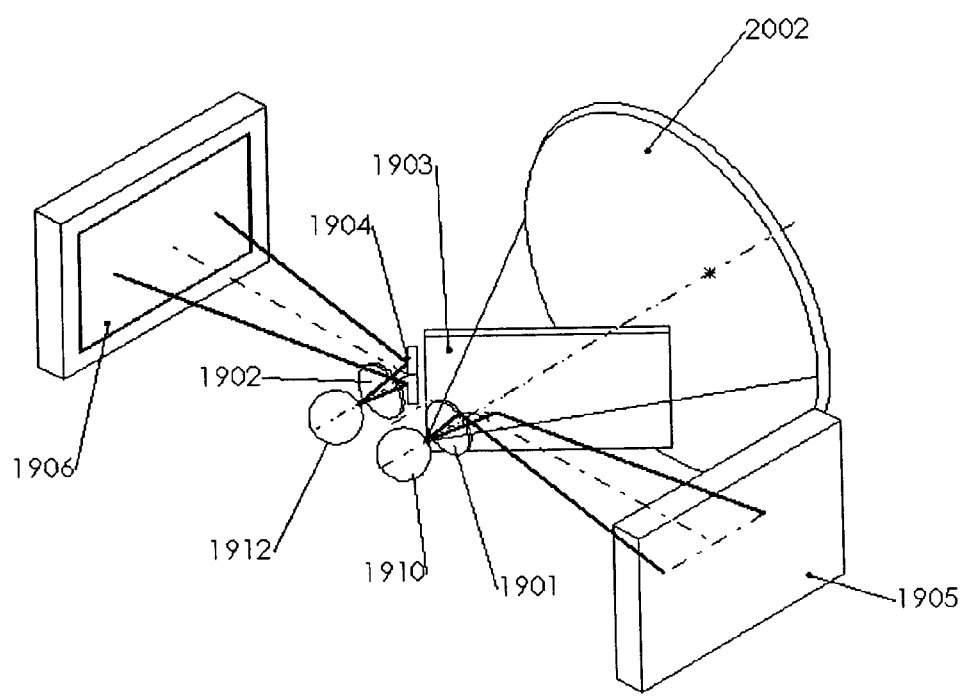
FIG. 20 is a schematic perspective view, showing additional optical elements of the visual field testing apparatus of FIG. 20.

With reference to FIG. 20, the eye under test 1910 views a curved screen 2002, whose radius is concentric with that of the eyeball as in the video projection system described above, and LCD panel 1905 through partial mirror 2 1903. The eye not under test 1912 views the LCD panel 1906 via reflective mirror 1904. This mirror 1904 for the eye not under test must have the same reflectivity as the partially reflecting mirror 1903 (so the images appear identical) yet is blackened on the backside so that light cannot transmit, thereby isolating the two fields of vision. The flashing test points can be achieved either by video projection described above, or by conventional means using a projected spot from a light source such as a laser or other suitable high intensity source.

Figure 21:
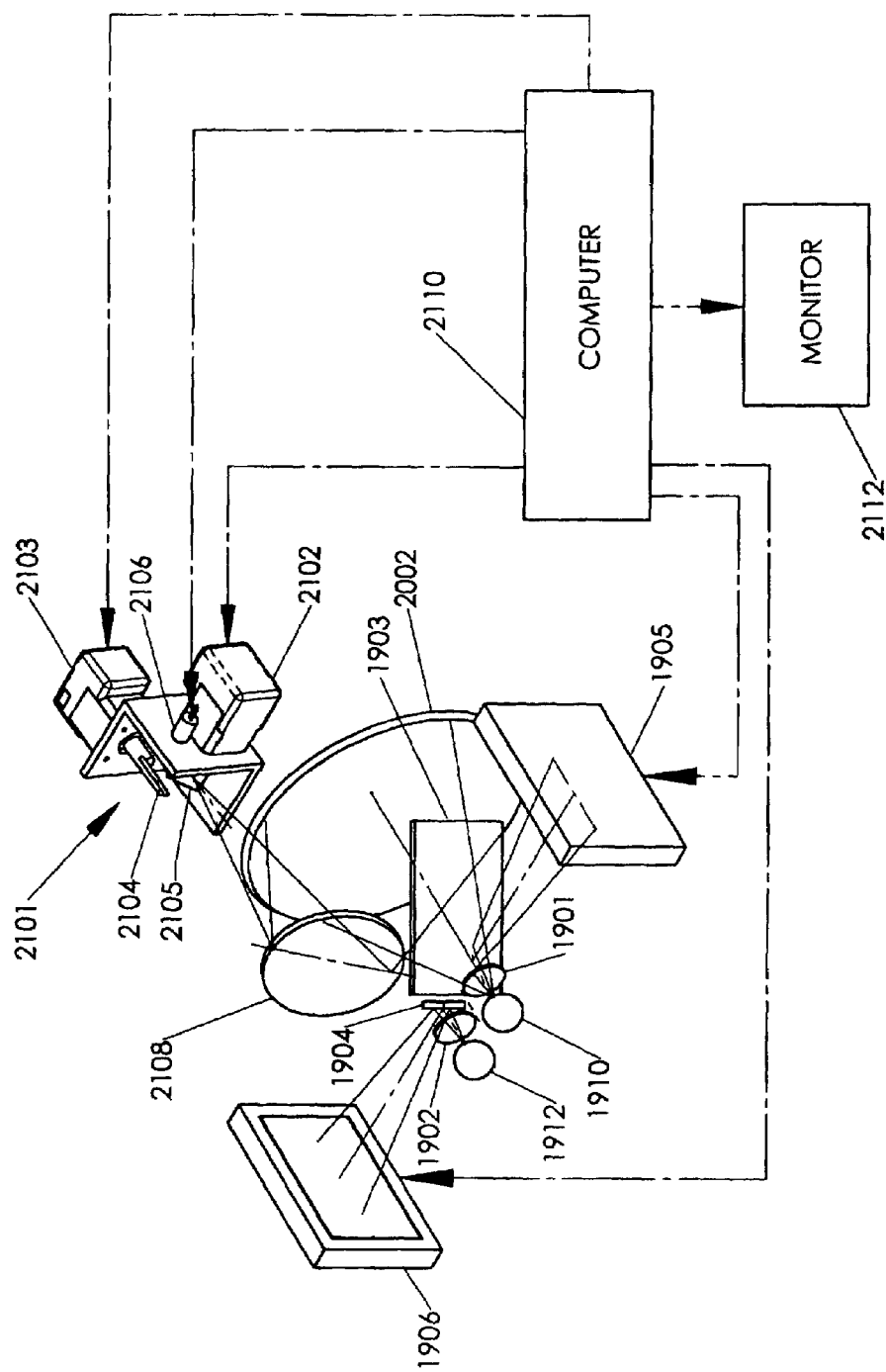
FIG. 21 is a schematic perspective view similar to FIG. 21, showing further optical elements of the visual field testing apparatus of FIGS. 20 and 21.

FIG. 21 shows the configuration of FIG. 20 with a 'flying' light spot which is presented throughout the field via a simple xy scanning system 2101. This system is made up of two computer-controlled motors 2102, 2103 with orthogonal mirrors 2104, 2105 mounted on shafts. A light source 2106 generates a well-defined spot of light which is variable in size and brightness on the curved screen 2002 after reflection from a fixed first surface fold mirror 2108.

During the test, a programmed host computer 2110 controls where on the curved screen 2002 the spot will land, the brightness, and the size, all variables set up by the operator before an examination. All of these variables, including test results as to which points were tested and which were seen are stored by programmed host computer 2110 and displayed after the test is complete on a separate computer monitor 2112 intended for viewing by the operator. Multiple video outputs each displaying a different video signal—one signal for each LCD panel and one for the monitor the operator views, is achieved with a triple output video card mounted in the host computer 2110 (for example, Matrox G450 MMS).

Figure 22:
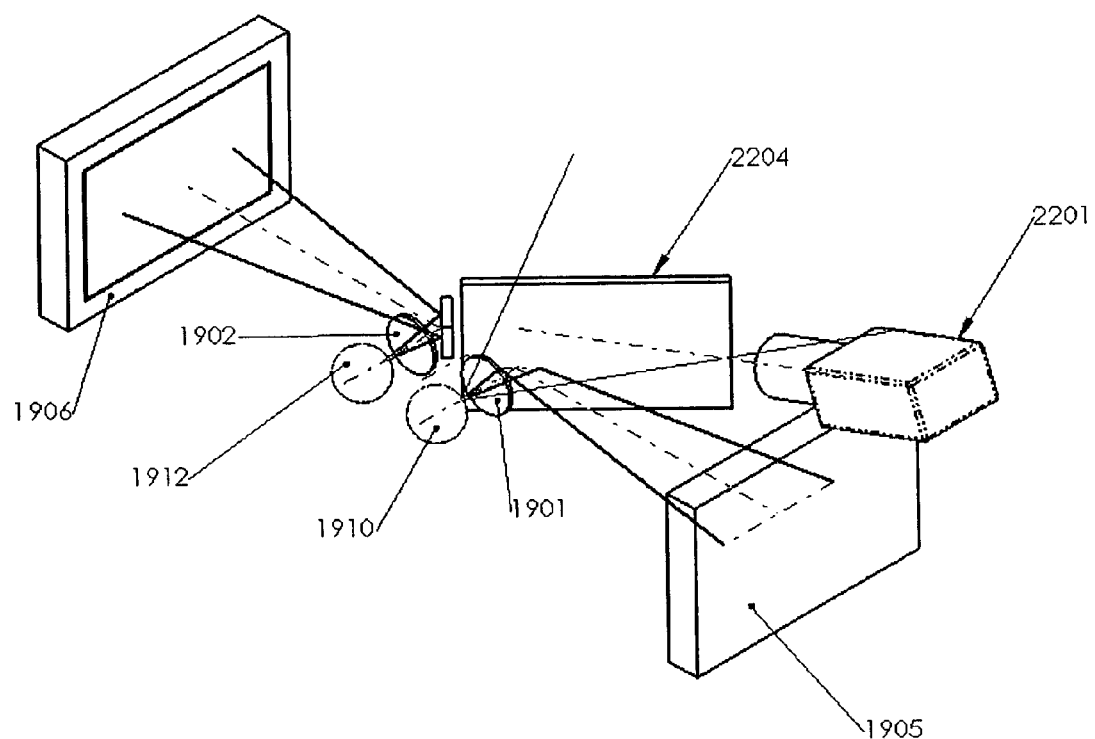
FIG. 22 is a schematic perspective view of the visual field testing apparatus of FIGS. 20 and 21, showing eyetracking optical elements in addition to elements depicted in FIGS. 20 and 21.

Eyetracking, which is necessary in any configuration for a reliable test, can be achieved in the system of FIG. 22 in several ways. Generally speaking, eyetracking as described herein uses a CCD camera to capture an image of the eye. Shown in FIG. 22, a CCD camera 2201 is mounted above the LCD panel 1905 so that an image of the eye under test 1910 is reflected off a partial mirror 2204 into the camera. Since the camera 2201 is disposed at a slight angle (off axis) this will cause a distortion of the image of the eye 1910, which is corrected in software.

Another modification to the system could be the use of "microdisplays" instead of conventional LCD panels. Microdisplays are produced by a number of companies (e.g., Kopin Corp., Cyberdisplay 640C), and are similar in operation to an LCD panel, however the image surface is generally produced by using thinned transparent silicon. The most notable difference in a microdisplay is the size of the active image area which measures approximately 6 mm×8 mm. Microdisplays are available in high resolution (640×480 pixels and higher) and in full color. If in the system shown in FIGS. 19-22, the LCD panels 1905, 1906 are replaced with microdisplays, additional optics are required to enlarge the microdisplay image for stereoscopic fusion. The main advantages of using microdisplays is their low cost (currently 10 times less expensive than LCD's of the same resolution) and their small size which will serve to compact the entire instrument.

Software

The software developed for the present invention serves several purposes. It operates the computer 114, 2110 to create the graphic fixation images on the computer display 100 or 200, the projection screen 806, 904, or 1015, or the LCD panels 1905 and 1906 that will appear three-dimensional and hold the patient's attention during the visual-field test procedure. The software allows the operator to adjust various parameters for the test and log the patient information such as name, date, diagnosis, etc. Under the control of the software, the computer 114, 2110 controls the performance of the chosen test and makes decisions during the test as to which points to test next to increase resolution. The software monitors input from the patient and from the eyetracker camera 604, 702, or 2201. After the test is complete, the software saves the data from the test performed, processes the data, and displays the results (e.g., on monitor 2112).

The software performs the actual testing of the patient by flashing test images at various points on the computer display 100, 200, 403, or 607 or the projection screen 806, 904, 1015, or 2002 and by recording responses from the patient to determine which points were visible. In the embodiment of FIG. 21, wherein laser light source 2106 is aimed at curved screen 2002 for illuminating test points, the software operates computer 2110 to control the brightness of the laser flash of laser 2106 through an analog-to-digital converter (not shown) and further controls the location of the flash by postioning mirrors 2104, 2105 that reflect the laser beam. Under the control of the software operating computer 2110, the two motors 2102 and 2103 rotate the mirrors 2105 and 2104, one for each axis. The software controls the motors 2102 and 2103 either through a serial port (not illustrated) or through commands to a dedicated motor-controller card (not illustrated) plugged into a slot of the computer 2110.

In the present form, the flashing points or test images generated on the computer display 100, 200, 403, or 607 or the projection screen 806, 904, 1015, or 2002 are available as squares or circles, are adjustable from ¼ of a degree up to 7 degrees in size (width and height), are available in varying intensities of white, blue, and red, and can flash for adjustable durations from half a second up to two seconds per light, for patients with slower reaction times. All these adjustments are chosen and set by the operator before beginning a test. The size of the flashing points is chosen in this range to accommodate patients with either low or high visual acuity, and could be certainly modified to include additional ranges if deemed necessary. This is true for the color of the flashing point as well, so that the color of the test points or images are not limited to these three hues, as the computer (e.g., 114 or 2110) is capable of producing colors numbering in the millions and any color could be added at any time.

The patient is instructed to press a hand-held button (not shown) or a key on the computer keyboard (not illustrated) whenever he sees a flash of light, and success or failure to detect each point is logged and stored by the software. During the test the software may remind the patient to keep fixating on the fixation image by playing recorded speech through a sound card of the control computer (114, 2110), much as a clinician would do during the administering of a standard visual field examination. The speech is played at timed intervals throughout the duration of the test, and is also played if the patient loses fixation which is detected via the eyetracker camera 604, 702, 2201. The speech is available in several different languages that are selectable at the beginning of the test. A second procedure may also be made available, whereby the patient hears a sound cue from the computer's speakers each time a point is flashed, and the patient must respond with a "yes" or "no" button to tell whether the point was seen. The computer 114, 2110 can then wait for either response before continuing. This procedure may be more convenient for patients who cannot respond as quickly to the test flashes. The pattern of points that are flashed depends upon the type of test chosen from the software menu.

The software is a Microsoft Windows™ based application program that includes a menu of the test options and a database form, and it runs on a personal computer. The computer 114, 2110 is comprised of a machine-readable data storage medium, a working memory for storing instructions for processing said machine-readable data, a central processing unit coupled to said working memory and to said machine-readable data storage medium for processing said machine readable data according to instructions given to it by the software of the present invention and a computer display or monitor 100, 200, 404, 607, 2112 coupled to said CPU for displaying the information to the user and the patient.

In several embodiments of the visual field testing apparatus described hereinabove, the software draws two binocularly displaced or stereoscopic fixation images or patterns for the patient to focus on during the test. This image or pattern covers the central area (i.e. 20°) for the eye under test and appears to the patient to be three dimensional when fused with the image presented to the other eye. The software further draws a small object, for instance a circle at the center of this pattern for fixation, to match a similar circle in the image presented to the eye not under test. The circle (e.g., 306 in FIGS. 3A-3C) will appear to float in front of the rest of the pattern due to the stereoscopic effect. In the cases where both images (eye under test and eye not under test) are displayed by computer 114, 2110, both fixation targets can be animated, to appear three-dimensional and in motion, which will help prevent the patient from losing fixation by letting the eyes wander.

Features in the complementary fixation images for the left and right eye must be offset to give the illusion of depth. Portions that are meant to appear closer to the viewer must be offset in each eye's image in the direction of the opposite eye, while the features that would appear more distant are centered closer to the axis of the eye viewing them. This mimics the effect of viewing a true solid object from the differing angles of two eyes. While the entire large (20 degree) fixation target has the three dimensional effect, the small central fixation object (e.g., 306) can also be three dimensional, representing a small cube for example. The animation of this object can incorporate the three dimensional effect to make parts of it move closer or farther away rather than just translationally. In other words, the cube appears to rotate, but does not change its location on the screen as in some existing perimeters. This along with slow changes in the coloring of the cube will help keep the patient's attention.

The software also draws a grid pattern over the whole testing area showing each one-degree and five-degree demarcation both horizontally and vertically. This grid allows the operator to see the location of the scotoma outlines more accurately, and to determine the size, shape, and extent of the scotoma in relation to the field of vision and is only drawn with the final results of the test, not while the test is under way.

The eyetracking software works by recording a picture of the patient's eye under test, with special attention to the dark pupil, as the eye under test looks at the center of the field before testing begins. The operator asks the patient to look directly at the fixation point and to open the eyes wide, to avoid interference in the baseline picture from eyelids or eyelashes. The actual shape and size of the pupil is recorded, as it can vary from a perfect circle. During the test the camera 604, 702, 2201 continuously takes pictures of the pupil and compares its location to the original, calibration or reference, location. A difference in pupil location greater than a threshold amount during the test causes a warning to be sent to the main visual-field testing software, which can pause until fixation is resumed, or restest the current point, or simply adjust the coordinates of the current tested point to compensate for the eye's new location. The allowable amount of variation in pupil location may be adjusted by the operator before the test or set by software to a standard value.

The procedure to determine the center of the pupil in the original baseline picture starts at the center of the picture, which must be somewhere inside the pupil, and records the average brightness of an area seven pixels wide and seven pixels high. The software then moves outward in increments of three pixels in all four directions, up, down, left, and right. It records the new average intensity at each step, and compares it to the average two steps previous (the second-to-last average) for greater contrast. An edge point of the pupil is defined as the location between the center and the edge of the picture where the average intensity increases by the greatest amount over two steps, since the pupil is the darkest feature of the picture. The geometric center of the four edge points found thus is used as the center of the pupil.

The shape of the pupil is then recorded, in the following manner. The software uses the same procedure for finding an edge point and repeats it up and down the left and right edges of the pupil at vertical increments of five or more pixels, to achieve a collection of points that constitute a dotted outline of the pupil. The top and bottom edges of the pupil, about ten to fifteen pixels in height, are neglected. The software then creates a variable array representing the intervals between each neighboring pair of points in the outline. It records in the array the linear slope between said neighboring points, along with the offset in horizontal and vertical pixels of the points from the center of the pupil previously calculated. The resulting variable array may be considered a group of tangents along each side of the pupil.

The purpose of the array of tangents is to allow the pupil to be located when it is partly obscured by eyelids or eyelashes. The algorithm for locating the pupil in real time during the test, which must be faster than the baseline algorithm to handle every frame from the camera without slowing down the main testing routine running concurrently on the processor, starts by searching the picture for any large dark area near the center that could be a portion of the pupil. It then uses the same edge-finding procedure to find two edge-points on each side of the dark region. The slope between the two edge points will equal the slope of the corresponding tangent in the array. Searching the array of tangents for the nearest matching slope will give the location on the baseline picture that corresponds to the location in question of the pupil in the real-time picture, since although the outline of the pupil may not be perfectly circular, it will rarely have a concavity (which would result in different locations of the edge having the same slope). As an example, for a perfectly circular pupil with a radius of 100 pixels, if the real-time algorithm found edge points on the lower left edge representing an angle of 135 degrees, or a slope of −1, the entry in the array would indicate that this section of the pupil corresponded to the portion in the original picture that was 71 pixels to the left and 71 pixels down from the center, since the sine of 135 degrees is 0.707, and the cosine is the negative of that.

It would not be accurate to conclude then that the center in the real time picture was 71 pixels to the right and above the left edge points found, because the pupil varies in size during a test. The right tangent at the same vertical coordinate in the circular pupil of the example would be located 142 pixels to the right of the left tangent that was used (2×71=142). The real time routine will have two edge points on the right edge of the pupil at the same height as the left segment. The horizontal distance between the right and left edge segments will tell how much the pupil has expanded or contracted as it varies from 142. If, in this example, this distance in the real-time picture is 120 pixels, then the pupil has contracted, and its center is be located 71×120/142=60 pixels to the right and 60 pixels above the midpoint of the two left edge points found.

This procedure of correlating the slope of the edge of the pupil to tangents of the pupil in the baseline picture allows the center of the pupil to be found even when only a thin horizontal section of the pupil is visible and the center itself is obscured by a drooping eyelid.

A final adjustment to the pupil's location may be necessary before the distance from perfect fixation may be calculated. Movement of the patient's head may be difficult to prevent even when the head is held in the chinrest by a strap. These movements can change the location of the pupil in the camera's frame even though the patient is still fixating. To compensate for these movements, the software uses the portion of the initial baseline picture extending from the bottom of the pupil downward to the bottom of the picture, and extending left and right to each end of the picture. This portion of the baseline picture will include the lower eyelid and eyelashes. The same portion of a sampling of the real time pictures will be compared to the initial picture to determine whether the entire head has moved.

The procedure to compare these regions is a convolution. The region from the real-time picture is converted by a Fourier Transform algorithm, and this transform is superimposed on the Fourier Transform of the region from the original picture. The location in the two dimensional array where the result is greatest tells the relative offset of one picture to the other. This well-know technique is used because of the complexity of the picture of the eyelid, with various eyelashes present. The edge-detecting technique described previously is successful for the simple shape of a curved pupil, but would not be practical for the eyelid. The technique of the Fourier Transform takes more time, and so can only be done in about one of six of the real-time pictures. This is acceptable because head movements are not as rapid as rotations of the eyeball, nor are they as temporary. A less-frequent test for head movements will still detect most of them.

The software includes a standard database form to record all typed information on each patient and keep it stored together with the data generated by each test. This typed information includes the patient's name, an identification number, the date of the test, diagnosis and operations or procedures the patient has undergone, and the name of the operator performing the test. The database includes menu buttons for creating new records, editing, saving, or deleting records, and navigating through all the records stored on disk.

The software may provide the operator many other options affecting the test that it will perform.

Some such options are listed below.

1. Buttons for OS (left eye) or OD (right eye) test.
2. Button to show missed points while the test is in progress or to hide them until the test is complete.
3. Points or line graphing: to show the results of a test only as points that were seen and that were not seen, or conversely to only curved lines describing approximated boundaries between seen and unseen points.
4. Flashed point sizes: seven options from small to large.
5. Three speeds or durations of the flashes: fast to slow
6. Colors and intensities for flashed test points: white, gray, blue, and red.
7. Type of fixation picture: three-dimensional circle or animated image.
8. Voice prompting: activates periodic prompting from the computer's sound card that reproduces a human voice telling the patient to continue to look at the fixation point at the center of the chart.
9. Point spacing: Determines how far apart the points in the predefined grid of test points will be spaced. A slider control allows adjustment from closer to wider.
10. Central area tests: three preset sizes of grids are available to test areas centered on the chart. The smallest extends 20° total in height and width, the next 35° total, and the largest 60°. The operator may also arbitrarily define any rectangular area for automatic testing by click the mouse at one corner of the desired area and dragging it to the other corner. Such user-defined test areas need not be centered in the test chart.
11. Quadrants to test: For any size of central area test chosen, a single quadrant (upper right is 1, upper left is 2, etc.) or quarter of the area may be tested, otherwise the full area will be tested when "All" is selected.
12. A peripheral test: as distinct from the central area tests, this test covers the outer edges of the chart to see how far the patient's peripheral vision extends. The peripheral test does not test the central areas.
13. A test labeled "AMD" to save time when testing patients with very large scotomas.
14. Blind-spot test: this test uses a small grid of test points covering the region where the physiological blind spot is expected, which region is about 22° to the temporal side of the center of the chart.
15. Manual test mode: with this type of test chosen, the operator may map out any location on the chart by indicating it with the computer's mouse pointer and clicking the left button on the mouse. Small areas may also be tested automatically by the computer when the operator moves the mouse pointer to the center of the desired area and presses the center button on a three-button mouse.
16. Start, Stop, and Pause buttons to control the test.
17. A Reset button to clear the chart before starting a test over.
18. A Print button to print out a chosen record from the database, including the full chart with seen and missed points.
19. A Hide Data button, to erase all buttons and the database from the display, leaving only the test chart while the test is in progress, to avoid distracting the patient.

Four basic types of tests are performed by the invented machine, and all are chosen from the button menu. The peripheral test finds how far the patient can see into the periphery or wide angles of his vision. This test starts with trial points near the edge of the monitor. Each time the patient fails to see a point, the computer moves the point closer to the center of vision and tries it again. When the patient has seen a point, the computer starts again from a different location on the perimeter and again moves inward until the patient sees the point. The final result is a series of lines radiating inward from the perimeter of the test field. The inner endpoints of those lines describe the outermost points the patient can see, or the limit of the patient's peripheral vision to all sides.

The second basic type of test is the manual test, wherein the operator specifies locations on the testing area by moving the cursor to them with the mouse, and flashes those test points by pressing the mouse button. This test allows complete flexibility for the operator should the patient have any odd visual defects that the software would not test well. The operator can also initiate an automated area test at the mouse's location from the manual test.

The third type of test, which is expected to be used most commonly, is the automated area test. The operator chooses the size of the area to be covered and the spacing distance of the predefined points to cover that area, which will depend on the accuracy required and the amount of time permissible for the test. The full automated test consists of testing a predefined grid of points that covers an intended area (with the software neglecting any points whose results can be assumed from surrounding points) and then going back to areas where points were missed and more accurately tracing the outline of the detected blind area or scotoma using points chosen to be more closely spaced.

The fourth basic test is designed for patients with large scotomas (i.e. greater than 25 degrees) like those that can be associated with diseases such as Age-related Macular Degeneration, retinal detachment, etc. It operates similarly to the third test as described above but instead tests the grid of points in a definite order rather than randomly. The fourth test procedure begins by testing a ring of grid points, in random order, all spaced between twenty and twenty-five degrees from the center point. The software then tests the next grid points closer to the center from the points in the original ring that were seen, but the grid points located directly inward from the points that were missed are skipped. The software continues moving inward in this pattern from all directions, stopping in any direction that reaches a missed point. The resulting pattern of missed points shows the edges of a large central blind area. The normal scotoma tracing routine is then invoked to outline the scotoma more accurately. This test is faster than a test of evenly-spaced points over the central area, because it does not have to test all the evenly-spaced grid points that would lie inside the blind area, all of which would be unseen by the patient anyway.

Testing the Predefined Grid

Figure 11:
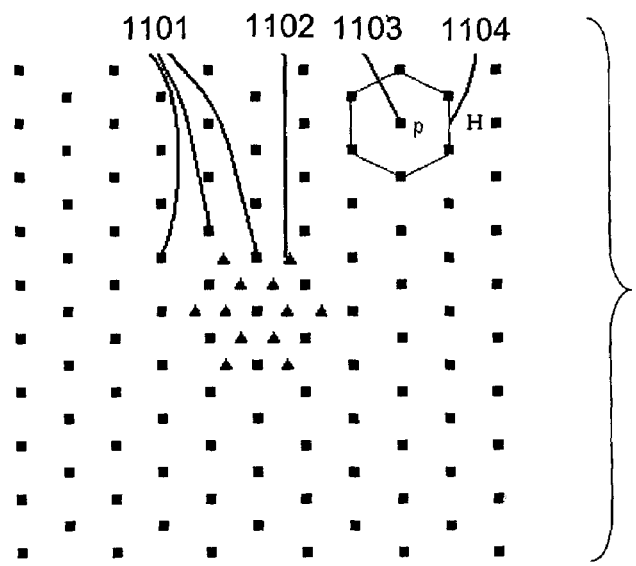
FIG. 11 is a diagram showing a hexagonal layout of test points displayed to a patient during a visual-field test in accordance with the present invention, and further showing a higher concentration of points near the center of the field.

A predefined grid of test points is set up around the central fixation point of the eye under test 104, 210, 418, 601, 907, the normal blind spot thereof, or in the case of manual mode tests, the location indicated by the mouse pointer. The central grid can be of various sizes, for example, from 10° to each side to 35° to each side. The central grid consists of regularly spaced points except at its center, near the central fixation point. More points are packed tightly together here, since the stereocampimeter of the present disclosure is especially designed for patients with loss of vision near the fixation point. In FIG. 11, all regularly spaced test points are shown as black squares 1101, while black triangles 1102 represent additional, more tightly packed test points near the center of the area to be tested.

As further illustrated in FIG. 11, the regularly spaced points 1101 are not laid out rectangularly, but in a staggered pattern, such that for any given point 1103, the nearest neighboring points form a perfect hexagon 1104. This pattern occurs in nature in the formation of crystals, and is referred to as the "hexagonal closest-packing" formation. Hexagonal packing is a more efficient arrangement of points, in the sense that there is less room for an area of lost vision to "hide" between the test points than a regular square arrangement would leave using the same number of points.

To test a point 1101, 1102 in one of these patterns, the computer 114, 2110 flashes a test image or light at the point and waits for the patient to press a key. The patient is instructed to press a key on the keyboard (or alternatively press a button connected to the serial port or some other input device) each time he sees a flash. The computer 114, 2110 tests the points in a random order, to keep the patient from guessing which point will come up next. The timing of the flashes is also somewhat random, to keep them unpredictable. If no key has been pressed within a given time, the computer 114, 2110 counts the point as missed and moves on. All points are tested, unless the computer 114, 2110 observes untested points completely surrounded by tested but unseen points. In these cases, it is safe to assume that points surrounded by scotoma are also part of the scotoma and will be unseen. After all points have been tested or assumed as misses without testing, the computer retests suspicious points. Suspicious points may be all points defining the boundary of seen and unseen regions, or all points whose neighbor points are mostly of the opposite status (seen or unseen), or simply all points that were unseen. Retesting points reduces the likelihood that they give false data because of patient error.

Grouping Missed Points and Counting the Groups

The region of a single scotoma, or area of non-vision, can cover many test points. To precisely trace all the scotomas in a particular portion of the visual field the computer 114, 2110 must know how many distinct scotomas are represented. For example, twenty missed test points may all lie together in one large scotoma, or they may represent three small scotomas that do not touch each other. Recognizing distinct groups among a chart of missed points is intuitive to a human but not trivial for computer logic.

The software uses two procedures to accomplish this grouping. The first grouping procedure creates groups of missed points that are contiguous; that is, all missed points that can be connected to each other without skipping over a "seen" point, are counted as a single group. Then a tracking procedure attempts to trace the outline of these groups. The second grouping procedure is not performed until after the tracking procedure. The second grouping procedure confirms or corrects the grouping that has been done by looking for any points that have not been encircled by the outlines already traced by the tracking procedure. If any such points are found the software initiates another tracking procedure to encircle those points.

Figure 18A:
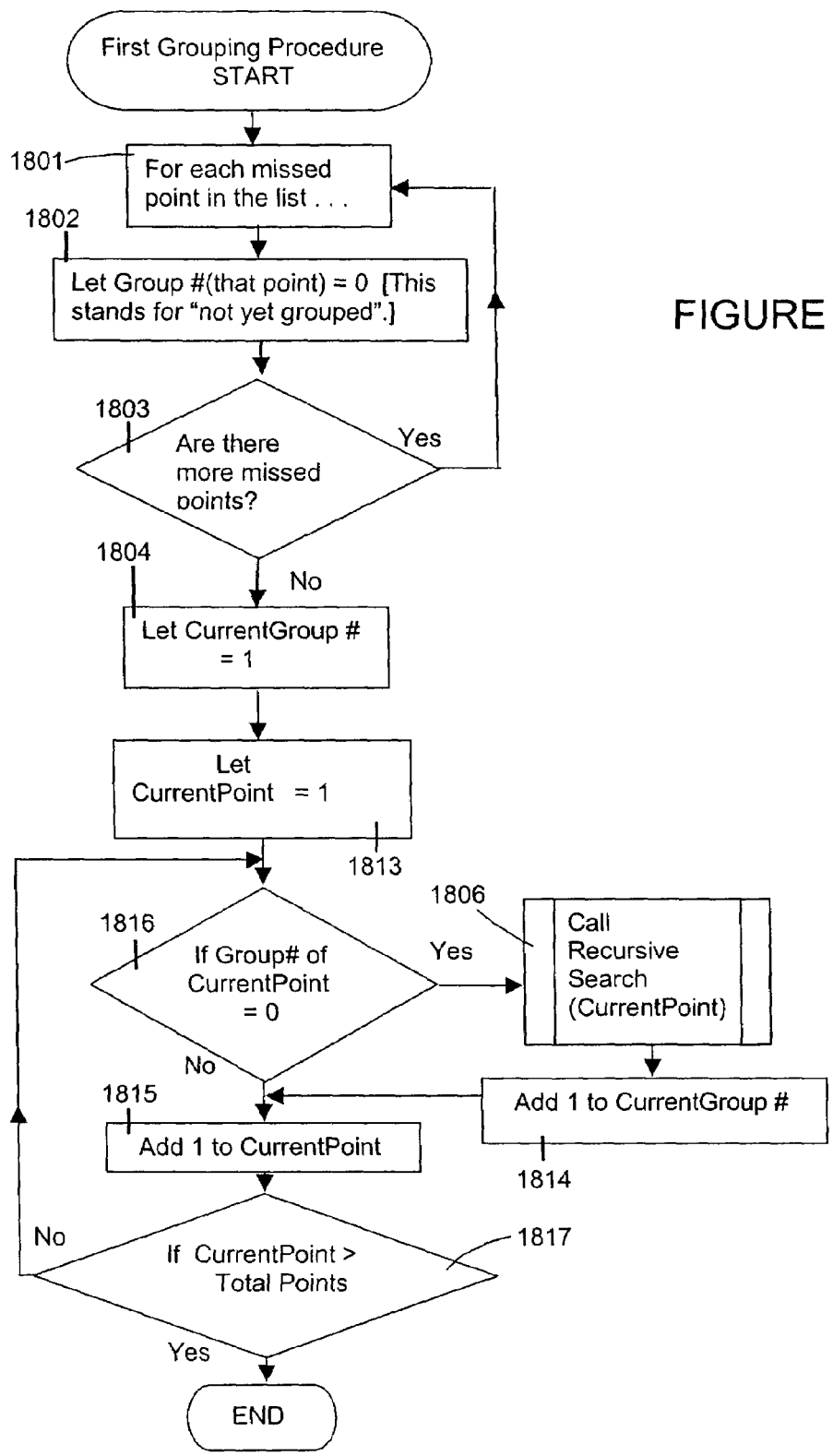
FIGS. 18A and 18B are flow chart diagrams showing steps in the grouping procedure algorithm (FIG. 13).
Figure 18B:
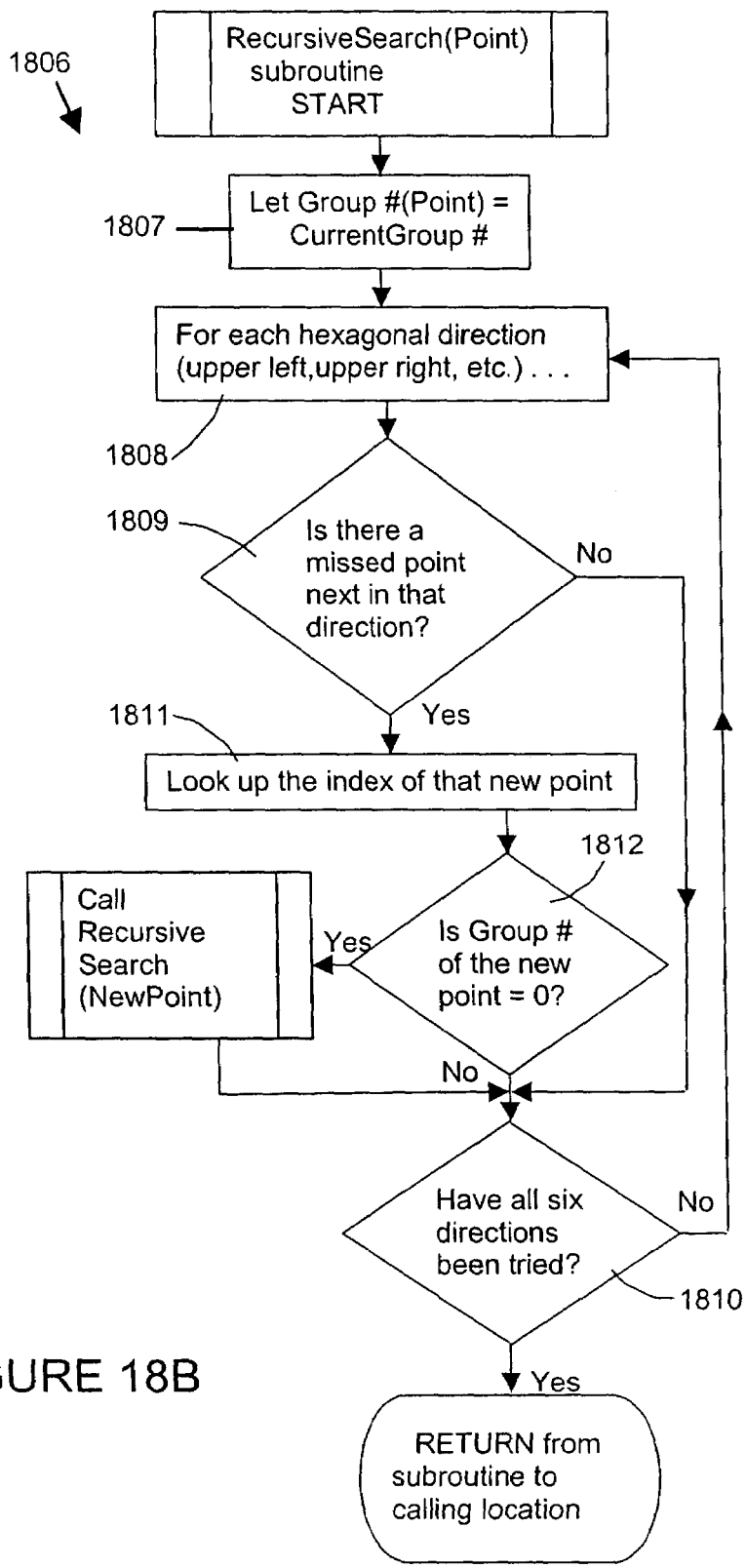

The first grouping and counting procedure is done by a recursive software routine depicted in flowchart form in FIG. 18A. The routine starts off at a step 1801 with a list of all "missed" points on the chart and marks all said points as being "ungrouped" or classified in a Group #0 (step 1802). The existence of further missed test points is checked at a decision junction 1803. The recursive routine then begins from any missed point and labels that point as a member of Group #1 in a step 1804. The routine then executes a subroutine 1806 that looks in each hexagonal direction from this point (up and left, straight up, up and right, down and right, down, down and left,) at the neighboring points (steps 1807, 1808 and decision junctions 1809 and 1810 in FIG. 18B). Any of these neighboring points that is missed, as determined in step 1811, and not labeled to a group (decision junction 1812) will also be marked as "Group #1." Then the software will take each of these points, in turn, and check each of its neighbors, and so on, in an expanding web (steps 1813-1815 and decision junction 1816). The routine ends when all directions have been checked from each missed point that has so far been included in Group #1, and no new missed points have been found to add to the group (step 1817). At this point the software has a set of contiguous points all labeled as members of Group #1. The software looks for any remaining missed evenly-spaced points from the list that have not yet been assigned to a group, and if the software finds any such missed points the group number is increased (to #2 in this case) and goes through the whole process again, finding neighbors to include in the group. When all the missed points from the original list have been assigned to groups, the procedure is done.

Figure 12:
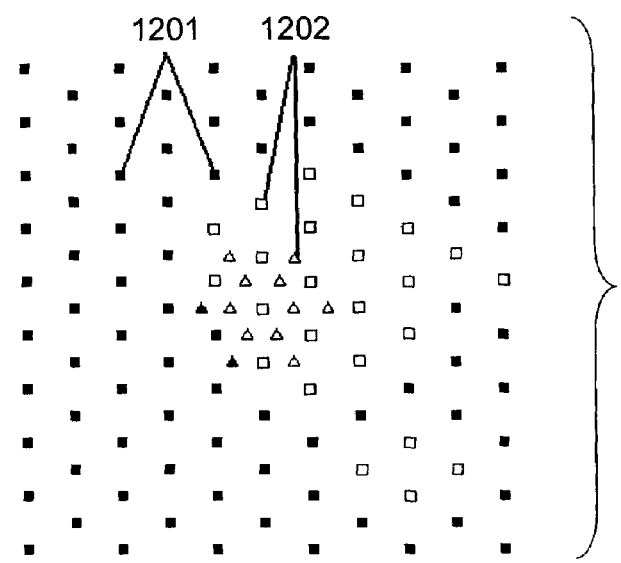
FIG. 12 is a diagram similar to FIG. 11, indicating illustrative preliminary results of visual-field testing in accordance with the present invention.
Figure 13:
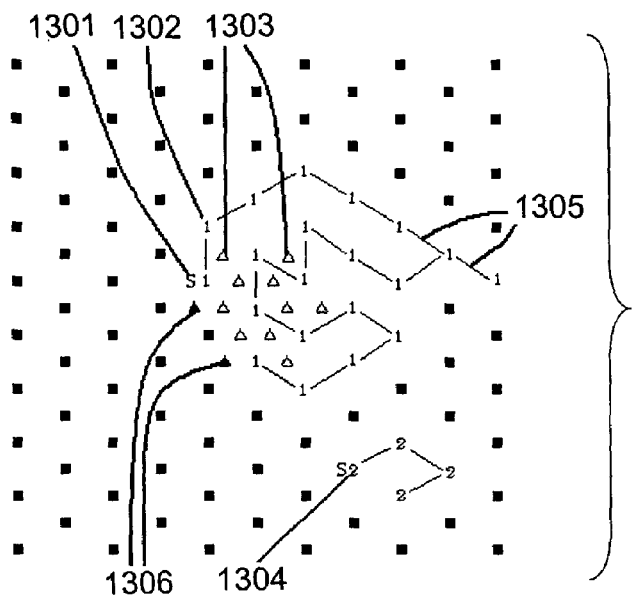
FIG. 13 a diagram similar to FIGS. 11 and 12, indicating a process performed by a first grouping procedure software algorithm in accordance with the present invention that groups missed points into distinct scotomas.

FIGS. 12 and 13 show an example of this process in action. FIG. 12 shows the preliminary results of testing before the grouping routine begins. Solid black points 1201 represent points the patient could see, and the hollow points 1202 show test points that the patient could not see. In FIG. 13, the first grouping procedure begins with point S1 1301. The routine looks to the upper left first, at the neighbor there, and sees that it is not a missed point. Then the grouping routine looks to the neighbor straight above and finds a missed point, and so labels it "1" 1302. Moving to this newly labeled point, the routine repeats the same steps, looking in all six directions for more missed points. The straight lines

1305 in FIG. 13 connect the points in the order that they are added to the group by the routine. The triangular points 1303 and 1306 in FIG. 13 still represent the more closely spaced test points 1102. The solid triangular points 1102 were seen but the hollow triangular points 1303 were unseen. They are not assigned to any group yet, because the first grouping procedure does not use them. Only the second grouping procedure can correctly assign these points, because of their irregular spacing.

When all the points labeled "1" have been reached, there are no more missed points to add to the group. This is because looking in all six directions from each point in the group, there are only points that are already included in the group, or points that the patient did not miss. Therefore Group #1 is complete. To see whether there are any more groups to find, the first grouping procedure then checks the list of regularly spaced missed points not the triangular points and in this example it does find points that have not yet been assigned to a group. The first grouping procedure starts arbitrarily from one of these points, (S2 in FIG. 13 (1304)) and performs the same grouping process again, which connects the four points labeled "2" in FIG. 13. The first grouping procedure again looks through the list of missed points and sees that all the missed evenly spaced points (hollow squares from FIG. 12) have been assigned a group number, so the first grouping procedure is complete.

Figure 14:
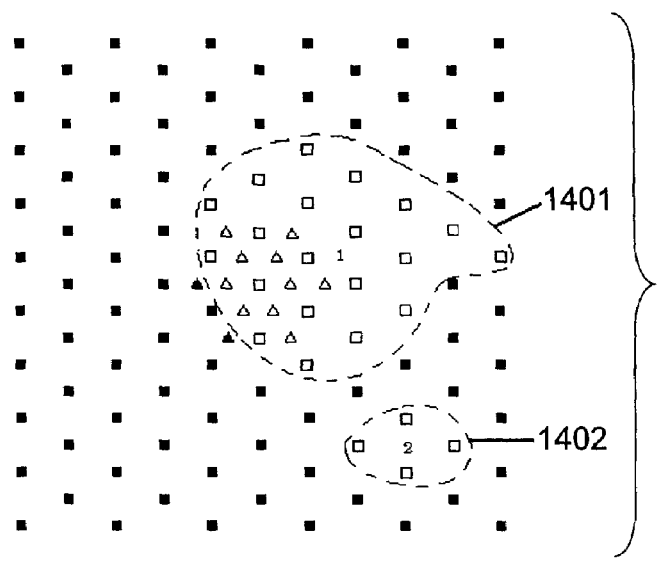
FIG. 14 a diagram similar to FIGS. 11-13, showing a computer's interpretation of the results of the first grouping procedure indicated in FIG. 13.

FIG. 14 shows the computer's interpretation of the results of the first grouping procedure. Two groups 1401, 1402 were found, so the computer 114, 2110 expects to find two scotomas. The dashed outlines surrounding the two groups 1401, 1402 are an approximation of the shape the computer 114, 2110 expects the scotomas to take. The software will now perform the tracing algorithm to locate the edges of the scotomas more precisely.

Defining the Perimeter of Each Group

Two methods are used to create a more accurate drawing of a defective area given a few unseen points from the previous procedure that lie inside it. When the area is estimated to be small, less than ten times the size of the test point itself in either direction, a filling procedure is used. This procedure simply tries points moving outward from the center of the defect area until it reaches an edge of the scotoma, where the patient can finally see the test flash. The procedure does this in all directions to find the complete outline, so that when done the defect area has been nearly filled with test points. For very small scotomas, this is an efficient method.

For all larger defects, a tracing procedure performs the task of accurately outlining the scotoma. This procedure involves the intelligent choosing of coordinates for points to be tested, based on results from the points immediately preceding, or "on the fly." No known devices use this technique to shorten the testing time or improve results. All current machines use a predefined layout of points; in other words, at the start of the test the operator can tell all the points that will have been tested at the end. The most sophisticated devices use algorithms to decide when to skip retests of some of the predefined points, to save time, but no conventional or previously existing machine actually defines new points to test as now described.

The tracking procedure chooses more points to test on the patient in order to define more accurately the edges of the scotomas identified by the first grouping procedure. To make this task easier, the software first estimates the size and shape of each scotoma. Using only the points assigned to the group being traced, the software calculates the maximum width and maximum height of the scotoma. This information will help it to predict how sharply the outline of the scotoma will curve along its length, so it can find any point on the edge in fewer attempts.

To trace the perimeter curve of the non-seeing area, the tracking procedure starts with a point that will be near the edge between visible and invisible areas. It tests the point midway between the left-most missed point of the group (point S1 1301 in FIG. 13), and the next point to the left of it, which was seen. If the patient can see this new test point, it chooses a point to the upper right next; otherwise it moves to the upper left. The tracking procedure continues testing new points farther to the left or right until it finds a point of the opposite status (seen or unseen) of the point tested just before it. This change in visible status, from seen to unseen or from unseen to seen, represents a crossing over the edge of the scotoma. The tracking procedure calculates the coordinates midway between the seen and unseen points and records this location as a transition point, or one of the points that lie on the edge of the scotoma. The tracking procedure then moves farther along the estimated edge of the scotoma, in a clockwise direction, and once again searches in the same way for a transition between visible and invisible points. The spacing of the new points that the tracking procedure tests is tighter than the spacing of the original grid points that were tested, to make the outlining more accurate. The tracking procedure does not necessarily follow the whole edge of the scotoma in a clockwise direction, but may jump ahead and back from time to time, filling in different sections of the outline until all the transition points are within a set distance of each other, which distance is smaller than the spacing of the original grid points and varies with the size of test spot in use. When no transition points are farther apart than this small distance, the outline is complete. This non-sequential tracing of the outline prevents the patient from predicting where the next point will be flashed, which could lead to false results.

If for any reason the routine that traces the scotoma meets with an error before it concludes (which means too many test points are consecutively seen or unseen, so there is no transition to locate the edge) the routine will back up three points before the last good transition, and retest the proceeding points. Usually false data in the preceding points (false positives or false negatives) leads the tracking routine away from the true edge to an area inside the scotoma, where all points will go unseen, or outside it where all will be seen, and retesting the three lead-in points will correct the error if true responses are given.

If the responses do not change, so that the error condition still exists, the routine will take the next option, which is to start back where tracing of the scotoma began, and proceed in the opposite direction of the original tracing (clockwise or counter-clockwise) around the scotoma. Then tracing ends not when the routine loops back to the starting point, but rather when it reaches the point where the edge was lost going in the first direction, as this will complete the loop.

The technique of returning to the starting point and tracing in the opposite direction is also used when an edge is lost because a scotoma extends past any edge of the test screen, or past the patient's peripheral vision. In this case the opposite tracing only continues until it also meets the edge of the screen or peripheral vision, and the outline of the scotoma will not be a closed loop.

Figure 15:
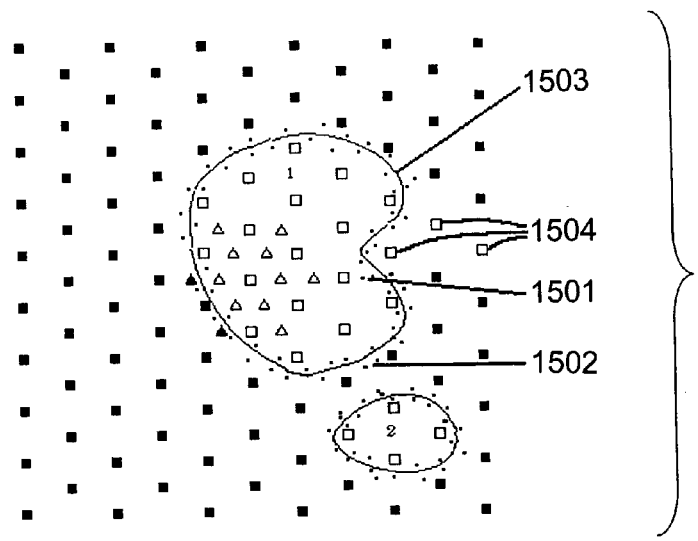
FIG. 15 a diagram similar to FIGS. 11-14, showing the results of a software algorithm tracking procedure in accordance with the present invention which defines more accurately the edges of the scotomas identified by the first grouping procedure (FIG. 13).

FIG. 15 shows the results of the tracking procedure for the example of FIGS. 11-14. The small dots represent the new points that the tracking procedure tested. Those points 1501 inside the curved outline 1503 are points the patient could not see, and the small dots 1502 outside the curved outline are points the patient did see. The midpoint between each of these pairs lies right on the outline, and outline itself 1503 is generated by a cubic-spline interpolation to connect all the midpoints. This outline may be drawn, for example, in blue for high visibility on one chart of the patient's results. Another chart might show no curve but only the points tried in the course of the test, in blue for missed points or white for seen points. This points-only chart can be considered the raw data of the test, and the chart with curved outlines could be considered enhanced or processed data. With the tracking procedure complete, the second grouping algorithm is now performed.

The Second Grouping Procedure

As FIG. 15 shows, the original grouping in this example is not entirely correct, because the first larger scotoma as outlined by the tracking procedure does not actually include three missed points 1504 on the far right that were assigned to Group #1. This means that there must actually be another scotoma that needs tracing. The job of the second grouping procedure is to account for each missed point of the original grid, to see whether it lies inside a traced outline, and if it does not, to find the new scotoma to which it belongs by initiating the previously described tracking algorithm yet again.

The algorithm to determine whether a given point lies within a closed curve is described in pseudocode below. The second grouping procedure creates two flag variables for each of the original missed points, one to tell whether the curved outline has passed over it called "Passed over" and the other to tell whether the outline has passed below it called "Passed under". Both variables start as false for each point. The software then steps along each segment of the curved outline in question in clockwise order around the scotoma, a segment being the space between neighboring transition points that originally generated the curve in the previous procedure. Each segment will cover a certain distance in the horizontal direction, or range of x-coordinates. For each segment, the software searches the entire list of original missed points to find any whose x-coordinates lie in that range. For every such point, if the segment passes above in y-coordinate and is moving rightward when moving from previous transition point to next then the variable Passed Over will be set to True. If the segment passes above but in a leftward direction when moving clockwise around the entire scotoma then the variable Passed Over will be set to False.

If the segment is below the missed point, and moves leftward, the variable Passed Under will be set True, but if the segment moves rightward Passed Under will be set False.

Figure 16:
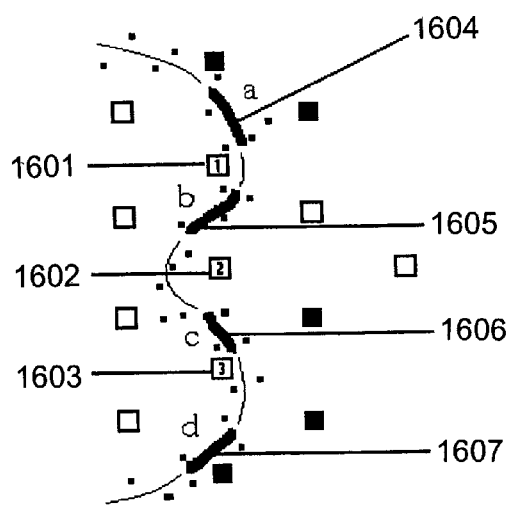
FIG. 16 is a close-up or detailed view of a concave section on the right side of a first scotoma shown in FIG. 15.

When the second grouping procedure has stepped through all the segments around a scotoma, all the original missed points that lie inside the outline of that scotoma will have both their Passed Over and Passed Under variables equal to True. Any points whose variables are not both True are not part of that scotoma. FIG. 16 shows a close-up of the concave section on the right side of the first scotoma from FIG. 15. This is the step-by-step description of how the second grouping procedure determines which of the missed points in FIG. 16 are part of the first scotoma:

The four important segments 1604-1607 of the scotoma outline are drawn in heavy black lines and labeled with the letters "a" through "d". The points 1601,1602, and 1603 that will be affected by them in the grouping algorithm are labeled 1, 2, and 3. The grouping algorithm moves clockwise around the whole outline, and this example starts when it reaches segment a 1604.

Segment a: The algorithm searches for all missed points whose x-coordinates lie between the left end of segment a and the right end. It finds the points 1, 2, and 3. Segment a lies above all three points, and is moving left to right, so the Passed Over variable for each point is set True.
  Passed Over(1)=True;
  Passed Over(2)=True;
  Passed Over(3)=True;
Segment b: The algorithm finds no points above or below the succeeding segments after a until it reaches segment b. It finds the same three points in the x-range of this segment.
  Point 1: The segment lies below this point and is moving right to left, so by the rules above:
    Passed Under(1)=True;
  Point 2: The segment is above this point but moving right to left, so
    Passed Over(2)=False;
  Point 3: The segment is above this point, moving right to left:
    Passed Over(3)=False;
Segment c: This segment is moving left to right again, and covers the range of the same three points.
  Point 1: The segment is under the point.
    Passed Under(1)=False;
  Point 2: The segment is under the point.
    Passed Under(2)=False;
  Point 3: The segment is over the point.
    Passed Over(3)=True;
Segment d: This segment moves right to left, and has the same relation to all three points since it is below them all.
  Passed Under(1)=True;
  Passed Under(2)=True;
  Passed Under(3)=True;

The algorithm then moves on to the segments past segment d, which move off to the left and so do not affect these three points or their variables. When the algorithm finishes the whole outline, it checks back on all the missed points and their flag variables. Some of the variables here have been changed from one value to another, but looking back at the last value each was given, we see:

| Passed Over(1) = True | Passed Over(2) = False | Passed Over(3) = True |
| Passed Under(1) = True | Passed Under(2) = True | Passed Under(3) = True |

Only when both variables are True for one point is it considered encircled, so that the algorithm sets:
Encircled(1)=True
Encircled(2)=True
Encircled(3)=True In other words, points 1 and 3 are inside the scotoma, but point 2 is not, as is obvious to a human observer looking at FIG. 16.

Figure 17:
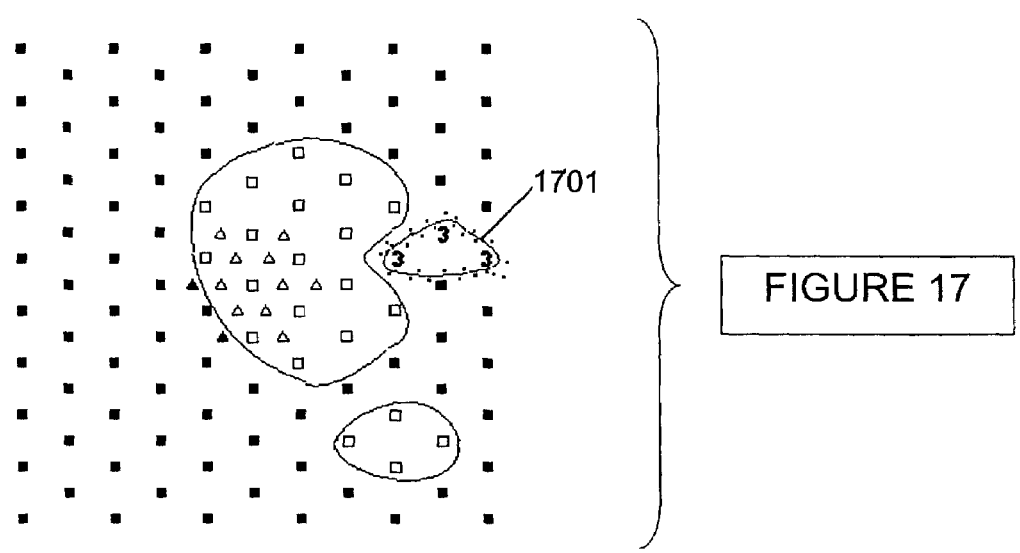
FIG. 17 a diagram similar to FIGS. 11-15, showing hypothetical results of the software algorithms in accordance with the present invention.

When the second grouping algorithm finishes, it finds point 2 was not inside the outline that was tracked. (The two missed points to the right of point 2 in FIG. 16 are also found to be outside, because their Passed Over and Passed Under variables would never have been changed from their original False settings, since the outline never reached over or under them.) Unencircled points indicate a separate scotoma, so the algorithm increments the scotoma number to three and initiates another tracking procedure just to the left of Point 2 (1602) in FIG. 16. The hypothetical results are shown in FIG. 17, with the new scotoma 1701 labeled "3." A repeat of the second grouping procedure would show all three previously unencircled points now encircled by the new outline, which shows that all scotomas have been outlined and all the procedures are done.

Thresholds

A scotoma is defined as a relative lack of visual sensitivity relative to the surrounding area. When a flashed test point is unseen by a patient, it may not indicate total blindness at that point of the retina, but rather reduced sensitivity, depending on the intensity of the test flash. The test procedures described above will find all the areas in the tested field of vision that fall below a given sensitivity, the sensitivity being selected by the operator before the test starts. By contrast, a perfect visual field test would tell the actual sensitivity of the retina at each point in the tested area. Most current commercial field testing devices find the sensitivity to within a set range or tolerance at various points in a pattern over the tested field. Then in displaying the data, these machines estimate the sensitivities between the tested points using mathematical interpolation. They do not create any sharply defined outlines.

A final technique of the current device is to outline scotomas, as described previously, at several sensitivities or thresholds. The machine will follow the procedures described to trace the outline of all areas where the patient's sensitivity falls below a level that will be estimated as near the midrange of sensitivities for that patient. Then the same procedure will be used with a lower and then a higher brightness in the test points, to create outlines that will run inside and outside the original outline. The result will then resemble a topographical map, wherein all points connected by a curved line share the same elevation. In this case, all points on the outline will share the same threshold of sensitivity. The software will find the second and third outlines more rapidly because it can predict that they will follow the same general shape of the initial outline, and therefore make fewer wrong guesses in choosing test points. It is also expected that they representation of the data will be more useful to physicians because changes in the patient's visual field over repeated visits will be more easily recognized.

It is to be noted that a great percentage of a patient's first visual field test is spent in merely locating scotomas before encircling them. Therefore time can be saved by using the previous test to direct test points when the same patient is tested at a later date, to check progress of the disease or treatments, for example. The software has a built-in feature that may be enabled when a patient is tested again. The feature takes the transition points of the outlines, which are stored separately by scotoma number in the database, averages their x and y coordinates to come up with an approximate geometric center of each scotoma, and concentrates testing on each center, skipping most of the grid points in the larger grid. The time saved in testing the wider grid points is used to trace the scotoma more accurately with more points without tiring the patient.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method for testing the visual field of a patient to determine an extent of at least one scotoma, comprising:
   measuring the visual perception of the patient by generating test images at a multiplicity of predetermined points on a visual field display viewed by the patient and recording the patient's responses to the test images to produce a set of raw data; and
   automatically analyzing said set of raw data to determine a closed curve generally separating points corresponding to unseen test images and points corresponding to seen test images, the analyzing of said raw data to determine said closed curve including:
   estimating a size and a shape of an area containing only points corresponding to unseen test images;
   based on the size and shape estimates, selecting a series of spaced points along a boundary of said area; and
   for each of said spaced points, more precisely determining the boundary of said area by automatically testing additional points located between points corresponding to unseen test images and points corresponding to seen test images.

2. The method defined in claim 1 wherein the more precise determining of said boundary includes selecting at least some of said additional points in dependence on the patient's responses to the testing of others of said additional points.

3. The method defined in claim 2 wherein the selecting of said additional points is executed automatically by a programmed computer.

4. The method defined in claim 1 wherein the more precise determining of said boundary includes measuring the visual perception of the patient at said additional points in the patient's visual field by generating respective test images at said additional points on said visual field display and recording the patient's responses to the respective test images to produce additional data pertaining to the visual field of the patient.

5. The method defined in claim 1 wherein said spaced points all correspond to test images unseen by the patient and wherein the more precise determining of said boundary includes for each selected one of said spaced points:
   (i) selecting a first additional point located between the respective selected spaced point and another tested point located outside said area;
   (ii) generating a first additional test image at said first additional point;
   (iii) recording the patient's response to said additional test image;
   (iv) selecting a second additional point located closer than said first additional point to said area where said additional test image is seen by the patient and farther from said area where said additional test image is unseen by the patient; and
   (v) continuing to select additional points for testing until two successively tested additional points test differently.

6. The method defined in claim 1 wherein said spaced points are taken from a group consisting of (a) the set of outermost unseen test points and (b) the set of innermost seen test points.

7. An apparatus for testing the visual field of a patient for scotomas, comprising:
- two display members located on opposite sides of a plane of symmetry extending through the patient's head;
- a computer operatively connected to said display members for generating binocularly displaced images of a common fixation object on said display members;
- at least two mirrors inclined at different angles with respect to one another for directing light rays from respective ones of said display members to respective ones of the patient's eyes, each of said mirrors being disposed along an optical axis of a respective eye of the patient, at least one of said mirrors being a beam splitting mirror;
- a projection screen located on a side of said beam splitting mirror opposite the patient; and
- a projector for projecting a test image onto said screen, said computer being operatively connected to said projector for controlling the generation of test images on said screen.

8. The apparatus defined in claim 7 wherein said computer is programmed to:
- measure the visual perception of the patient by operating said projector to project test images onto said screen at a multiplicity of predetermined points;
- record the patient's responses to the test images to produce a set of raw data;
- automatically analyze said set of raw data to determine a closed curve generally separating points corresponding to unseen test images and points corresponding to seen test images;
- define a series of spaced points along said curve; and
- for each of said spaced points, more precisely determine a boundary between points corresponding to unseen test images and points corresponding to seen test images, by automatically testing additional points in a region located about said curve and between points corresponding to unseen test images and points corresponding to seen test images.

9. The apparatus defined in claim 8 wherein said computer is further programmed to select at least some of said additional points in dependence on the patient's responses to the testing of others of said additional points.

10. The apparatus defined in claim 7 wherein said display members are LCD display screens.

11. The apparatus defined in claim 7 wherein said display members substantially face one another.

12. The apparatus defined in claim 7 wherein said computer is programmed to generate a series of differentially displaced binocular images of said common object on said display members, so that said object is a three-dimensional moving object.

13. A method for testing the visual field of a patient, comprising:
- generating on a test display area a series of test images at different points of the patient's visual field;
- recording the patient's responses to said test images;
- during the generating of said test images, generating, on a pair of spaced display areas, two binocularly displaced images of a fixation object so that said fixation object appears to the patient to be three dimensional and in motion; and
- analyzing the patient's response to said test images to map scotomas of the patient's visual field.

14. The method defined in claim 13 wherein said fixation object is taken from the group consisting of a geometric form and an animated figure.

15. The method defined in claim 14 wherein said display members are located on opposite sides of a sagittal plane through the patient.

16. The method defined in claim 13 wherein the generating of said binocularly displaced images includes operating a computer to energize a pair of display members.

17. A method for testing the visual field of a patient, comprising:
- presenting stereoscopic or binocularly displaced fixation images to the respective eyes of the patient;
- producing a series of test images viewable by only one of the patient's eyes;
- operating a computer to generate said fixation images and said test images;
- operating said computer to record the patient's responses to said test images to produce a set of raw data; and
- operating said computer to analyze said raw data to map scotomas of the patient's visual field.

18. The method defined in claim 17 wherein the presenting of said fixation images includes energizing two separate electronic displays.

19. The method defined in claim 18 wherein the producing of said test images includes producing images on a third display member different from said electronic displays.

20. The method defined in claim 18 wherein said displays are LCD panels.

21. The method defined in claim 17 wherein operating said computer to analyze said raw data includes operating said computer to
- analyze said set of raw data to determine a closed curve generally separating points corresponding to unseen test images and points corresponding to seen test images.

22. The method defined in claim 21 wherein the operating of said computer to automatically determine said closed curve includes executing a computer routine or program to:
- estimate a size and a shape of an area containing only points corresponding to unseen test images;
- based on the size and shape estimates, select a series of spaced points along a boundary of said area; and
- for each of said spaced points, more precisely determine the boundary of said area by automatically testing additional points located between points corresponding to unseen test images and points corresponding to seen test images.

23. The method defined in claim 22 wherein the operating of said computer to more precisely determine said boundary includes operating said computer to automatically select at least some of said additional points in dependence on the patient's responses to the testing of others of said additional points.

24. The method defined in claim 17 wherein the presenting of said stereoscopic or binocularly displaced fixation images to the patient includes generating said stereoscopic or binocularly displaced fixation images on a pair of spaced display areas during the generating of said test images so that said fixation object appears to the patient to be three dimensional and in motion.

25. A method for testing the visual field of a patient, comprising:
- presenting a fixation image to at least one eye of a patient;
- producing a series of test images viewable by said eye;
- operating a computer to generate said fixation image and said test images;
- recording the patient's responses to said test images; and
- analyzing the patient's response to said test images to map scotomas of the patient's visual field, the presenting of said fixation image and the producing of said test images including the projection of video images from video displays onto at least one screen.

26. A method for testing the visual field of a patient, comprising:

presenting a fixation image to an eye of a patient;

producing a series of test images to the patient;

recording the patient's responses to said test images; and analyzing the patient's response to said test images to map scotomas of the patient's visual field, wherein said fixation image is substantially brighter than said test images, said test images being produced on a display, the presenting of said fixation image including (a) moving a light source separate from said display from a first position out of optical alignment with said display to a position in optical alignment with said display and said eye, and (b) energizing said light source.

27. The method defined in claim 26 wherein said display includes a projection screen and said light source is a diode.

28. The method defined in claim 26 said second position is between said display and said eye and said first position is not between said display and said eye.

29. The method defined in claim 26 wherein said test images are produced so as to be viewable said eye.

30. The method defined in claim 26 wherein said eye is an eye under test, said test images being produced said as to be viewable only by an eye of the patient other than said eye under test.

31. A method for testing the visual field of a patient, comprising:

measuring the visual perception of the patient by generating test images at a multiplicity of predetermined points on a visual field display viewed by the patient and recording the patient's responses to the test images to produce a set of raw data; and automatically analyzing said set of raw data to define an area of the patient's eye containing solely points corresponding to unseen test images, the analyzing of said raw data to determine said area including testing other points in the visual field of the patient, said other points being selected depending on the patient's prior response to test images.

* * * * *